(12) United States Patent
Daoud

(10) Patent No.: US 6,719,779 B2
(45) Date of Patent: Apr. 13, 2004

(54) CIRCULATION SET FOR TEMPERATURE-CONTROLLED CATHETER AND METHOD OF USING THE SAME

(75) Inventor: Adib Gabrail Daoud, San Diego, CA (US)

(73) Assignee: Innercool Therapies, Inc., San Diego ( * ) Notice: Subject to any disclaimer, the term of this patent is extended or adjusted under 35 U.S.C. 154(b) by 45 days.

(21) Appl. No.: 10/007,545

(22) Filed: Nov. 6, 2001

(65) Prior Publication Data

US 2002/0116041 A1 Aug. 22, 2002

Related U.S. Application Data

(60) Provisional application No. 60/247,203, filed on Nov. 7, 2000.

(51) Int. Cl.[7] .................................................. A61F 7/00
(52) U.S. Cl. ........................ 607/105; 607/96; 607/113
(58) Field of Search ........................ 607/96, 104, 105, 607/113

(56) References Cited

U.S. PATENT DOCUMENTS

| 2,308,484 A | 1/1943 | Auzin et al. |
| 2,374,609 A | 4/1945 | McCollum |
| 2,615,686 A | 10/1952 | Davidson |
| 2,672,032 A | 3/1954 | Towse |
| 2,913,009 A | 11/1959 | Kuthe |
| 3,298,371 A | 1/1967 | Lee |
| 3,425,419 A | 2/1969 | Dato |
| 3,504,674 A | 4/1970 | Swenson et al. |
| 3,865,116 A | 2/1975 | Brooks |

(List continued on next page.)

FOREIGN PATENT DOCUMENTS

| AU | 685559 B2 | 1/1998 |
| CA | 2177982 | 6/1995 |
| CN | 1082382 A | 2/1994 |
| EP | 0655225 A1 | 5/1993 |
| EP | 0 664 990 | 11/1997 |
| EP | 428505 B2 | 3/2001 |

(List continued on next page.)

OTHER PUBLICATIONS

DeFord, J.A., et al.; Design and Evaluation of Closed–Loop Feedback Control of Minimum Temperatures in Human Intracranial Tumours Treated with Interstitial Hyperthermia; Med. & Biol. Eng. & Comput., vol. 29, pp. 197–206 (Mar. 1991).

Ambrus; The Biphasic Nature and Temperature Dependence of the Activation of Human Plasminogen by Urokinase; May 1979; pp. 339–347; Research Communications in Chemical Pathology and Pharmacology, vol. 24, No. 2.

(List continued on next page.)

*Primary Examiner*—Roy D. Gibson
(74) *Attorney, Agent, or Firm*—Mark D. Wieczorek

(57) ABSTRACT

The invention provides a single-use, disposable circulation set for a heat transfer catheter. The circulation set includes a single-use, disposable fluid reservoir adapted to supply a heat transfer fluid to the catheter, a single-use, disposable pump adapted to pump heat transfer fluid through the catheter from the fluid reservoir, a single-use, disposable filter assembly adapted to remove impurities from the heat transfer fluid, a single-use, disposable heat exchanger member adapted for use with a heat exchanger for transferring heat between the heat exchanger and the fluid, a single-use, disposable temperature and pressure sensor block member for use with a multi-use, non-disposable temperature and pressure sensor electronics member, a single-use, disposable supply line communicating the fluid reservoir, pump, filter assembly, heat exchanger, and temperature and pressure sensor block member, and adapted to be connected to the catheter for supplying heat transfer fluid to the catheter, and a single-use, disposable return line communicating the temperature and pressure sensor block member and fluid reservoir, and adapted to be connected to the catheter for returning heat transfer fluid to the fluid reservoir.

58 Claims, 10 Drawing Sheets

U.S. PATENT DOCUMENTS

| | | |
|---|---|---|
| 3,888,259 A | 6/1975 | Miley |
| 3,971,383 A | 7/1976 | Van Gerven |
| 4,038,519 A | 7/1977 | Foucras |
| 4,127,365 A | 11/1978 | Martin et al. |
| 4,153,048 A | 5/1979 | Magrini |
| 4,165,206 A | 8/1979 | Martin et al. |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,375,941 A | 3/1983 | Child |
| 4,391,029 A | 7/1983 | Czuba et al. |
| 4,427,009 A | 1/1984 | Wells et al. |
| 4,445,500 A | 5/1984 | Osterholm |
| 4,483,341 A | 11/1984 | Witteles |
| 4,493,625 A | 1/1985 | Pieters |
| 4,502,286 A | 3/1985 | Okada et al. |
| 4,562,414 A | 12/1985 | Linder et al. |
| 4,569,355 A | 2/1986 | Bitterly |
| 4,581,017 A | 4/1986 | Sahota |
| 4,585,056 A | 4/1986 | Oscarsson |
| 4,602,642 A | 7/1986 | O'Hara et al. |
| 4,655,746 A | 4/1987 | Daniels et al. |
| 4,672,962 A | 6/1987 | Hershenson |
| 4,731,072 A | 3/1988 | Aid |
| 4,739,492 A | 4/1988 | Cochran |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,129 A | 8/1988 | Bonzel |
| 4,762,130 A | 8/1988 | Fogarty et al. |
| 4,781,033 A | 11/1988 | Steyert et al. |
| 4,789,000 A | 12/1988 | Aslanian |
| 4,796,640 A | 1/1989 | Webler |
| 4,806,182 A | 2/1989 | Rydell |
| 4,820,349 A | 4/1989 | Saab |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,917,687 A | 4/1990 | O'Boyle |
| 4,920,963 A | 5/1990 | Brader |
| 4,951,677 A | 8/1990 | Crowley et al. |
| 4,962,761 A * | 10/1990 | Golden ..................... 607/104 |
| 4,964,409 A | 10/1990 | Tremulis |
| 5,000,734 A | 3/1991 | Boussignac et al. |
| 5,002,531 A | 3/1991 | Bonzel |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,059,057 A | 10/1991 | Graef |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishwara et al. |
| 5,108,390 A | 4/1992 | Potocky et al. |
| 5,110,721 A | 5/1992 | Anaise et al. |
| 5,117,822 A | 6/1992 | Laghi |
| 5,129,887 A | 7/1992 | Euteneuer et al. |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,174,285 A | 12/1992 | Fontenot |
| 5,180,896 A | 1/1993 | Gibby et al. |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,226,286 A | 7/1993 | Mo |
| 5,234,405 A | 8/1993 | Klatz et al. |
| 5,234,413 A | 8/1993 | Wonder et al. |
| 5,241,951 A | 9/1993 | Mason et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,284,423 A | 2/1994 | Holdsworth et al. |
| 5,306,261 A | 4/1994 | Alliger et al. |
| 5,310,440 A | 5/1994 | Zingher |
| D347,890 S | 6/1994 | Eads |
| D348,101 S | 6/1994 | Poli et al. |
| 5,320,503 A | 6/1994 | Davis |
| 5,322,514 A | 6/1994 | Steube et al. |
| 5,322,515 A | 6/1994 | Karas et al. |
| 5,322,518 A | 6/1994 | Schneider et al. |
| 5,324,319 A | 6/1994 | Mason et al. |
| 5,326,165 A | 7/1994 | Walthall et al. |
| 5,326,166 A | 7/1994 | Walthall et al. |
| 5,326,236 A | 7/1994 | Kramer et al. |
| 5,328,461 A | 7/1994 | Utterberg |
| 5,330,435 A | 7/1994 | Vaillancourt |
| 5,330,438 A | 7/1994 | Gollobin et al. |
| 5,330,519 A | 7/1994 | Mason et al. |
| 5,331,309 A | 7/1994 | Sakai |
| 5,332,399 A | 7/1994 | Grabenkort et al. |
| 5,334,179 A | 8/1994 | Poli et al. |
| 5,334,180 A | 8/1994 | Adolf et al. |
| 5,334,182 A | 8/1994 | Simons et al. |
| 5,334,188 A | 8/1994 | Inoue et al. |
| 5,334,193 A | 8/1994 | Nardella |
| 5,334,197 A | 8/1994 | Kriesel et al. |
| 5,336,190 A | 8/1994 | Moss et al. |
| 5,339,511 A | 8/1994 | Bell |
| 5,340,290 A | 8/1994 | Clemens |
| 5,342,181 A | 8/1994 | Schock et al. |
| 5,342,182 A | 8/1994 | Montoya et al. |
| 5,342,301 A | 8/1994 | Saab |
| 5,342,346 A | 8/1994 | Honda et al. |
| 5,342,347 A | 8/1994 | Kikuchi et al. |
| 5,343,734 A | 9/1994 | Maeda et al. |
| 5,344,436 A | 9/1994 | Fontenot et al. |
| 5,346,466 A | 9/1994 | Yerlikaya et al. |
| 5,352,213 A | 10/1994 | Woodard |
| 5,354,186 A | 10/1994 | Murtuza et al. |
| 5,354,264 A | 10/1994 | Bae et al. |
| 5,354,272 A | 10/1994 | Swendson et al. |
| 5,364,364 A | 11/1994 | Kasvikis et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |

| | | |
|---|---|---|
| 5,443,456 A | 8/1995 | Alliger et al. |
| 5,462,521 A | 10/1995 | Brucker et al. |
| 5,466,131 A | 11/1995 | Altham et al. |
| 5,486,204 A | 1/1996 | Clifton |
| 5,486,208 A | 1/1996 | Ginsburg |
| 5,496,271 A | 3/1996 | Burton et al. |
| 5,514,094 A | 5/1996 | Anello et al. |
| 5,531,776 A | 7/1996 | Ward et al. |
| 5,549,559 A | 8/1996 | Eshell |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,609,591 A * | 3/1997 | Daikuzono .................. 606/15 |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,647,051 A | 7/1997 | Neer |
| 5,653,692 A | 8/1997 | Masterson et al. |
| 5,702,234 A | 12/1997 | Pieters |
| 5,709,654 A | 1/1998 | Klatz et al. |
| 5,713,941 A | 2/1998 | Robins et al. |
| 5,716,386 A | 2/1998 | Ward et al. |
| 5,733,318 A | 3/1998 | Augustine |
| 5,733,319 A | 3/1998 | Neilson et al. |
| 5,735,809 A | 4/1998 | Gorsuch |
| 5,741,248 A | 4/1998 | Stern et al. |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,807,391 A | 9/1998 | Wijkamp |
| 5,824,030 A | 10/1998 | Yang et al. |
| 5,827,222 A | 10/1998 | Klatz et al. |
| 5,827,237 A | 10/1998 | Macoviak et al. |
| 5,827,269 A | 10/1998 | Saadat |
| 5,833,671 A | 11/1998 | Macoviak et al. |
| 5,837,003 A | 11/1998 | Ginsburg |
| 5,861,021 A | 1/1999 | Thome et al. |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,963 A | 9/1999 | Dobak, III |
| 5,971,979 A | 10/1999 | Joye et al. |
| 5,989,238 A | 11/1999 | Ginsburg |
| 6,019,783 A | 2/2000 | Philips et al. |
| 6,022,336 A | 2/2000 | Zadno-Azizi |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A * | 11/2000 | Noda et al. .................. 607/105 |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |
| 6,194,899 B1 | 2/2001 | Ishihara et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,287,326 B1 | 9/2001 | Pecor |
| 6,290,697 B1 | 9/2001 | Tu et al. |
| 6,290,717 B1 | 9/2001 | Philips |
| 6,299,599 B1 | 10/2001 | Pham et al. |
| 6,303,156 B1 | 10/2001 | Ferrigno |
| 6,306,161 B1 | 10/2001 | Ginsburg |
| 6,312,452 B1 | 11/2001 | Dobak, III et al. |
| 6,315,995 B1 | 11/2001 | Pinsky et al. |
| 6,316,403 B1 | 11/2001 | Pinsky et al. |
| 6,325,818 B1 | 12/2001 | Werneth |
| 6,338,727 B1 | 1/2002 | Noda et al. |
| 6,432,102 B2 | 8/2002 | Joye et al. |
| 6,527,798 B2 | 3/2003 | Ginsburg et al. |
| 6,530,946 B1 | 3/2003 | Noda et al. |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |
| 2001/0007951 A1 | 7/2001 | Dobak, III |
| 2001/0008975 A1 | 7/2001 | Dobak, III et al. |
| 2001/0009610 A1 | 7/2001 | Augustine et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0014802 A1 | 8/2001 | Tu |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0031946 A1 | 10/2001 | Walker et al. |
| 2001/0032004 A1 | 10/2001 | Werneth |
| 2001/0039440 A1 | 11/2001 | Lasheras et al. |
| 2001/0041923 A1 | 11/2001 | Dobak, III |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0116041 A1 | 8/2002 | Daoud |
| 2003/0045917 A1 | 3/2003 | Noda et al. |
| 2003/0060761 A1 | 3/2003 | Evans et al. |

FOREIGN PATENT DOCUMENTS

| | | |
|---|---|---|
| EP | 1159019 B1 | 11/2002 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |

| | | |
|---|---|---|
| WO | WO 99/04211 | 1/1999 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 01/03606 | 1/2000 |
| WO | WO 00/09054 | 2/2000 |
| WO | WO 01/08580 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/53246 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/87379 | 5/2001 |
| WO | WO 01/95840 | 5/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 02/07793 | 1/2002 |
| WO | WO 02/13710 | 2/2002 |
| WO | WO 02/26285 | 4/2002 |
| WO | WO 02/26307 | 4/2002 |

OTHER PUBLICATIONS

Bigelo; Hypothermia, Its Possible Role in Cardiac Surgery; Nov. 1959; pp. 849–866; Annals of Surgery, vol. 132, No. 5.

Cheatle; Cryostripping the Long and Short Saphenous Veins; Jan. 1993; one page; Br. J. Surg., vol. 80.

Dexter; Blood Warms as It Blows Retrograde from a Femoral Cannulation Site to the Carotid Artery During Cardiopulmonary Bypass; Nov. 1994; pp. 393–397; Perfusion, vol. 9, No. 6.

Gillinov; Superior Cerebral Protection with Profound Hypothermia During Circulatory Arrest; Nov. 1992; pp. 1432–1439; Ann. Thorac. Surg., vol. 55.

Higazi; The Effect of Ultrasonic Irradiation and Temperature on Fibrinolytic Activity in Vitro; Aug. 1992; pp. 251–253; Thrombosis Research, vol. 69, No. 2.

Imamaki; Retrograde Cerebral Perfusion with Hypothermic Blood Provides Efficient Protection of the Brain; Jul. 1995; pp. 325–333; Journal of Cardiac Surgery, vol. 10, No. 4, Part 1.

Jolin; Management of a Giant Intracranial Aneurysm Using Surface–Heparinized Extracorporeal Circulation and Controlled Deep Hypothermic Low Flow Perfusion; Aug. 1992; pp. 756–760; Acta Anaesthesiologica Scandinavia.

Jos R.C. Jansen, Ph.D., et al., (1997) Near continuous cardiac output by thermodilution. Journal of Clinical Monitoring 13:233–239.

Kimoto; Open Heart Surgery under Direct Vision with the Aid of Brain–Cooling by Irrigation; Jul. 1955; pp. 592–603; Surgery, vol. 39, No. 4.

Marekovic, Z.; Abstract of Renal Hypothermia in Situ by Venous Passages: Experimental Work on Dogs; 1980; Eur Urol 6(2); 1 page.

Meden; Effect of Hypothermia and Delayed Thrombolysis in a Rat Embolic Stroke Model; Dec. 1993; pp. 91–98; Acta Neurologica Scandinavica.

Meden; The Influence of Body Temperature on Infarct Volume and Thrombolytic Therapy in a Rat Embolic Stroke Model; Feb. 1994; pp. 131–138; Brain Research, vol. 647.

Milleret, Rene; La cryo–chirurgie danes les varices des mimbres inferieurs; Angiologie; Supplement au No. 110.

Milleret; Abstract of Cryosclerosis of the Saphenous Veins in Varicose Reflux in the Obese and Elderly; 10.1981; one page; Phlebologie, vol. 34, No. 4.

Parkins, Brain Cooling in the Prevention of Brain Damage During Periods of Circulatory Occlusion in Dogs, Apr. 1954; pp. 284–289; Annals of Surgery, vol. 140, No. 3.

Piepgras; Rapid Active Internal Core Cooling for Induction of Moderate Hypothermia in Head Injury by Use of an Extracorporeal Heat Exchanger; Feb. 1998; pp. 311–318; Neurosurgery, vol. 42, No. 2.

Rijken; Plasminogen Activation at Low Temperatures in Plasma Samples Containing Therapeutic Concentrations of Tissue–Type Plasminogen Activator or Other Thrombolytic Agents; Oct. 1989; pp. 47–52; place of publication unknown.

Schwartz, A.E. et al.; (1996); Isolated cerebral hypothermia by single carotid artery perfusion of extracorporeally cooled blood in baboons; Neurosurgery 39(3):577–582.

Schwartz; Cerebral Blood Flow during Low–flow Hypothermic Cardiopulmonary Bypass in Baboons; Jun. 1994; pp. 959–964; Anesthesiology, vol. 81, No. 4.

Schwartz; Selective Cerebral Hypothermia by Means of Transfemoral Internal Carotid Artery Catheterization; May 1996; pp. 571–572; Radiology, vol. 201, No. 2.

Steen; The Detrimental Effects of Prolonged Hypothermia and Rewarming in the Dog; Aug. 1979; pp. 224–230; Anesthesiology, vol. 52, No. 3.

Vandam; *Hypothermia*; Sep. 1959; pp. 546–553; The New England Journal of Medicine.

White; Cerebral Hypothermia and Circulatory Arrest; Jul. 1978; pp. 450–458; Mayo Clinic Proceedings, vol. 53.

Yenari; Thrombolysis with Tissue Plasminogen Activator (TPA) is Temperature Dependent; Jul. 1994; pp. 475–481; Thrombosis Research, vol. 77, No. 5.

Yoshihara; Changes in Coagulation and Fibrinolysis Occurring in Dogs during Hypothermia; Aug. 1984; pp. 503–512; Thrombosis Research, vol. 37, No. 4.

Zarins; Circulation in Profound Hypothermia; Nov. 1972; pp. 97–104; Journal of Surgical Research, vol. 14, N.2.

Acton, J. C., L. C. Sheppard, N.T. Kouchoukos, J. W. Kirklin, Automated Care Systems for Critically III Patients Following Cardiac Surgery, Dept. of Surgery, University of Alabama in Birmingham, Birmingham, Alabama 35294, pp. 111–115.

Anon, Automatic Feedback Instrumentation for Hospital Room Utilizing Microsensors, IBM Technical 'Disclosure Bulletin, Aug., 1986, vol. 29 (3):1320.

Carrol, D. L., C. Finn, S. Gill, J. Sawyer, adn B. Judge, A Comparison of Measurements from a Trmporal Artery of Thermomter nd a Pulmonary Artery Thermistor—Preliminary Results.

Colvett, K. T. et al. Opportunities with Combined Modality Therapy for Selective Organ Preservation in Muscle–Invasive Bladder Cancer, J. Surg. Oncology 1996; 63:201–208.

DeFord, et al. Design and Evaluation of Closed–Loop Feedback Control of Minimum Temperatures in Human Intracranial Tumours Treated with Interstitial Hyperthermia, Med. & Biol. Eng. & Comput. 1991, 29:197–206.

Hayes, et al. Temperature Control in Extracorporeal Circulation, New Appliances, Aug. 17, 1988, p. 430.

Maas, C. et al. Intermittent Antegrade/Selective Cerebral Perfusion during Circulatory Arrest for Repair of the Aortic Arch, Perfusion 1997; 12:;127–132.

Olshausen et al. An Isothermal Flowmeter with Improved Frequency Response for Measuring Tissue Blood Flow, 1976, Pflügers Arch., 2367:97–102.

Sessler, D. I., Temperature–Monitoring and Thermal Management Guidelines, Anesthesiology 1998; 89:1298–300.

Shiraki, K. et al. Esophageal and Tympanic Temperature Responses to Core Blood Temperature Changes during Hyperthermia, J. Appl. Physiol. 1986; 61(1):98–102.

Health Devices; "Gorman–Rupp Hypothermia Machine"; vol. 1; pp. 190–191 (Nov. 1971–Apr. 1972).

Health Devices; "Gorman–Rupp Hypothermia Machine"; pp. 263–265 (Jul.–Aug. 1972).

* cited by examiner

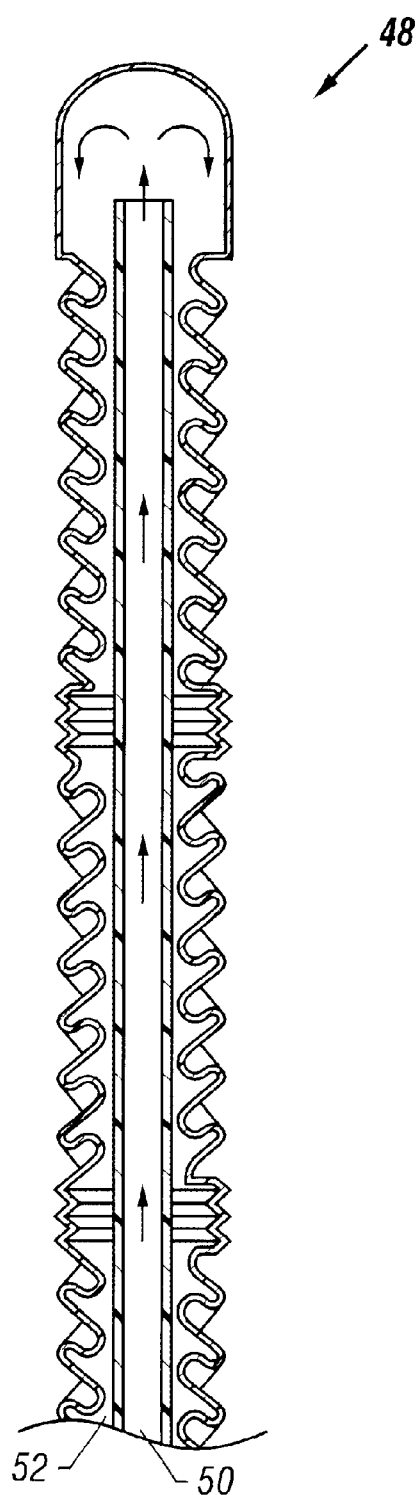
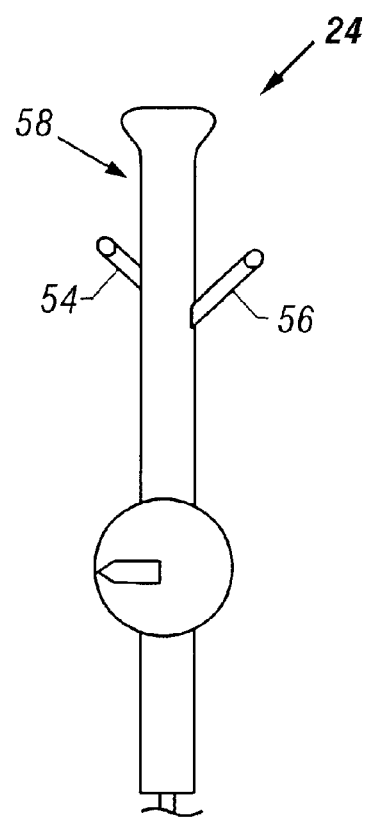
*FIG. 2A*  *FIG. 2B*

CIRCULATION SET FOR TEMPERATURE-CONTROLLED CATHETER AND METHOD OF USING THE SAME

RELATED APPLICATIONS

This application is a Provisional-to-Utility Conversion of and claims priority to U.S. application Ser. No. 60/247,203, entitled "Improved Circulation Set for Temperature-Controlled Catheter and Method of Using Same," filed on Nov. 7, 2000.

BACKGROUND OF THE INVENTION

1. Field of the Invention

The present invention relates, in general, to a circulation set for a temperature-controlled catheter and, in particular, to a circulation set for a hypothermia catheter.

2. Background Information

Numerous catheters exist for non-invasive treatment of a variety of internal areas and regions of a patient. Many of these catheters circulate a fluid through a distal portion of the catheter. An example of a type of catheter that may circulate fluid through a distal portion of the catheter is a hypothermia catheter. A hypothermia catheter is inserted into the bloodstream of a patient in order to induce partial or total body hypothermia. A hypothermia catheter may be used to reduce the effects of certain bodily injuries to the brain as well as other organs. A hypothermia catheter may include a heat transfer element located at a distal portion of the catheter. A heat transfer fluid may be circulated along an internal portion of the heat transfer element, drawing heat from the heat transfer element. This, in turn, causes heat to be removed from blood flowing along an external surface of the heat transfer element, causing the resulting blood to be cooled. The collective components that supply fluid to the catheter and regulate the temperature of the fluid being delivered to and/or returning from the distal portion are referred to herein as the circulation set and may include one or more of the following: a fluid reservoir, a pump, a filter, a heat exchanger, a temperature sensor, a pressure sensor, and tubing.

The inventors of the present invention have recognized that as health insurance companies constantly cut back on the amount they are willing to pay for medical devices used in medical procedures, it important to produce a quality circulation set made of inexpensive components. Drawbacks of circulation sets in the past are that many or all of the components of the set are made of relatively expensive non-disposable components intended to be used numerous times before being disposed of, any disposable components of the circulation set are not conveniently separable from the non-disposable components, and the disposable components that are used are not made of readily-available cheap components. The inventors of the present invention have also recognized that it would be better for insurance reimbursement purposes if the circulation set was made of relatively inexpensive components and was essentially disposable.

SUMMARY OF THE INVENTION

A first aspect of the invention involves a single-use, disposable circulation set for a heat transfer catheter. The circulation set includes a single-use, disposable fluid reservoir adapted to supply a heat transfer fluid to the catheter, a single-use, disposable pump adapted to pump heat transfer fluid through the catheter from the fluid reservoir, a single-use, disposable filter assembly adapted to remove impurities from the heat transfer fluid, a single-use, disposable heat exchanger member adapted for use with a heat exchanger for transferring heat between the heat exchanger and the fluid, a single-use, disposable temperature and pressure sensor block member for use with a multi-use, non-disposable temperature and pressure sensor electronics member, a single-use, disposable supply line communicating the fluid reservoir, pump, filter assembly, heat exchanger, and temperature and pressure sensor block member, and adapted to be connected to the catheter for supplying heat transfer fluid to the catheter, and a single-use, disposable return line communicating the temperature and pressure sensor block member and fluid reservoir, and adapted to be connected to the catheter for returning heat transfer fluid to the fluid reservoir.

A second aspect of the invention involves a single-use, disposable circulation set for a catheter. The circulation set includes a single-use, disposable fluid reservoir adapted to supply a heat transfer fluid to the catheter, a single-use, disposable heat exchanger member adapted for use with a heat exchanger for transferring heat between the heat exchanger and the fluid, a single-use, disposable temperature and pressure sensor block member for use with a multi-use, non-disposable temperature and pressure sensor electronics member, a single-use, disposable supply line communicating the fluid reservoir, heat exchanger, and temperature and pressure sensor block member, and adapted to be connected to the catheter for supplying heat transfer fluid to the catheter, and a single-use, disposable return line communicating the temperature and pressure sensor block member and fluid reservoir, and adapted to be connected to the catheter for returning heat transfer fluid to the fluid reservoir.

A third aspect of the invention involves a single-use, disposable circulation set for a catheter. The circulation set includes a single-use, disposable fluid reservoir adapted to supply a heat transfer fluid to the catheter, a single-use, disposable temperature and pressure sensor block member for use with a multi-use, non-disposable temperature and pressure sensor electronics member, a single-use, disposable supply line communicating the fluid reservoir and temperature and pressure sensor block member, and adapted to be connected to the catheter for supplying heat transfer fluid to the catheter, and a single-use, disposable return line communicating the temperature and pressure sensor block member and fluid reservoir, and adapted to be connected to the catheter for returning heat transfer fluid to the fluid reservoir.

A fourth aspect of the invention involves a single-use, disposable circulation set for a catheter. The circulation set includes a single-use, disposable fluid reservoir adapted to supply a heat transfer fluid to the catheter, a single-use, disposable heat exchanger member adapted for use with a heat exchanger for transferring heat between the heat exchanger and the fluid, a single-use, disposable supply line communicating the fluid reservoir and heat exchanger, and adapted to be connected to the catheter for supplying heat transfer fluid to the catheter, and a single-use, disposable return line communicating with the fluid reservoir, and adapted to be connected to the catheter for returning heat transfer fluid to the fluid reservoir.

A fifth aspect of the invention involves a single-use, disposable circulation set for a catheter. The circulation set includes a single-use, disposable heat exchanger member adapted for use with a heat exchanger for transferring heat between the heat exchanger and the fluid, a single-use, disposable temperature and pressure sensor block member for use with a multi-use, non-disposable temperature and pressure sensor electronics member, a single-use, disposable supply line communicating the heat exchanger and temperature and pressure sensor block member, and adapted to be connected to the catheter for supplying heat transfer fluid to the catheter, and a single-use, disposable return line communicating with the temperature and pressure sensor block member, and adapted to be connected to the catheter for returning heat transfer fluid from the catheter.

A sixth aspect of the invention involves a method of using a circulation set for a heat transfer catheter. The method includes attaching a single-use, disposable circulation set including a fluid reservoir, a pump, a heat exchanger member, a condition sensor member, supply line, and return line to the catheter, circulating heat transfer fluid and controlling the temperature of the same through the catheter with the circulation set, and disposing the circulation set after a single use.

A seventh aspect of the invention involves a method of using a circulation set for a heat transfer catheter. The method includes providing a single-use, disposable circulation set for the catheter, the circulation set comprising a single-use, disposable fluid reservoir adapted to supply a heat transfer fluid to the catheter, a single-use, disposable pump adapted to pump heat transfer fluid through the catheter from the fluid reservoir, a single-use, disposable filter assembly adapted to remove impurities from the heat transfer fluid, a single-use, disposable heat exchanger member adapted for use with a multi-use, non-disposable heat exchanger for transferring heat between the heat exchanger and the fluid, a single-use, disposable temperature and pressure sensor block member for use with a multi-use, non-disposable temperature and pressure sensor electronics member, a single-use, disposable supply line communicating the fluid reservoir, pump, filter assembly, heat exchanger, and temperature and pressure sensor block member, and adapted to be connected to the catheter for supplying heat transfer fluid to the catheter, and a single-use, disposable return line communicating the temperature and pressure sensor block member and fluid reservoir, and adapted to be connected to the catheter for returning heat transfer fluid to the fluid reservoir; connecting the return line and supply line to the catheter; coupling the single-use, disposable temperature and pressure sensor block member with the multi-use, non-disposable temperature and pressure sensor electronics member; coupling the single-use, disposable heat exchanger member with the multi-use, non-disposable heat exchanger; circulating heat transfer fluid and controlling the flow rate and temperature of the same through the catheter with the pump, heat exchanger, and the temperature and pressure sensor block member and electronics member; and disposing the circulation set after a single use.

An eighth aspect of the invention involves a disposable fluid reservoir for supplying a heat transfer fluid to a circulation set of a heat transfer catheter, the circulation set including a supply line for supplying heat transfer fluid to the heat transfer catheter for fluid circulation purposes and a return line for returning heat transfer fluid to the fluid reservoir for fluid circulation purposes. The fluid reservoir includes an intravenous ("IV") bag normally used for the intravenous delivery of one or more fluids to the vasculature of a patient, the bag including a top and a bottom, an inlet line located within the bag and adapted to communicate with the return line for returning fluid to the bag during circulation, and an outlet line located within the bag and adapted to communicate with the supply line for supplying fluid to the catheter during circulation.

A ninth aspect of the invention involves a fluid reservoir for supplying a heat transfer fluid to a circulation set of a heat transfer catheter, the circulation set including a supply line for supplying heat transfer fluid to the heat transfer catheter for fluid circulation purposes and a return line for returning heat transfer fluid to the fluid reservoir for fluid circulation purposes. The fluid reservoir includes a fluid reservoir body including a top and a bottom, an air-removal mechanism located in the body near the top of the body, an inlet line including an outlet located within the body, the inlet line adapted to communicate with the return line for returning fluid to the body during circulation, an outlet line including an inlet located at least partially within the body, the outlet line adapted to communicate with the supply line for supplying fluid to the catheter during circulation, and wherein the outlet of the inlet line is located closer to the air-removal mechanism than the inlet of the outlet line.

A tenth aspect of the invention involves a method of using a fluid reservoir in a circulation set for a heat transfer catheter, the circulation set including a supply line for supplying heat transfer fluid to the catheter for fluid circulation purposes and a return line for returning heat transfer fluid to the fluid reservoir for fluid circulation purposes. The method includes using intravenous ("IV") bag normally used for the intravenous delivery of one or more fluids to the vasculature of a patient as a fluid reservoir in a circulation set for a heat transfer catheter, an inlet line located within the IV bag and adapted to communicate with the return line for returning fluid to the IV bag during circulation, and an outlet line located within the IV bag and adapted to communicate with the supply line for supplying fluid to the catheter during circulation; circulating heat transfer fluid from the catheter through the return line, into the inlet line, through the IV bag, out the outlet line, and through the supply line to the catheter; and disposing the IV bag after a single use.

An eleventh aspect of the invention involves a method of using a fluid reservoir in a circulation set for a heat transfer catheter, the circulation set including a supply line for supplying heat transfer fluid to the catheter for fluid circulation purposes and a return line for returning heat transfer fluid to the fluid reservoir for fluid circulation purposes. The method includes providing a fluid reservoir, the fluid reservoir including a fluid reservoir body, an air-removal mechanism located in the body, an inlet line including an outlet located within the body, the inlet line adapted to communicate with the return line for returning fluid to the body during circulation, an outlet line including an inlet located at least partially within the body, the outlet line adapted to communicate with the supply line for supplying fluid to the catheter during circulation, and wherein the outlet of the inlet line is located closer to the air-removal mechanism than the inlet of the outlet line; circulating heat transfer fluid from the catheter through the return line, into the inlet line, through the fluid reservoir body, out the outlet line, and through the supply line to the catheter; and removing air from the circulation set with the air-removal mechanism.

A twelfth aspect of the invention involves a temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from the catheter for fluid circulation purposes. The temperature and pressure sensor assembly includes a multi-use, non-disposable temperature and pressure sensor electronics member, and a single-use, disposable temperature and pressure sensor block member removably coupled to the electronics member so that the block member may be discarded after a single use and the electronics member may be used multiple times with different disposable block assemblies, the block member adapted to communicate with the supply line and return line.

A thirteenth aspect of the invention involves a single-use, disposable temperature and pressure sensor block member of a temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from the catheter for fluid circulation purposes. The temperature and pressure sensor block member includes a single-use, disposable temperature and pressure sensor block member adapted to be removably coupled to a multi-use, non-disposable temperature and pressure sensor electronics member so that the block member may be discarded after a single use and the electronics member may be used multiple times with different disposable block assemblies. The block member includes a pressure sensor hole adapted to communicate with a supply lumen and receive a pressure sensor of the electronics member, a temperature sensor hole adapted to communicate with the supply lumen and receive a temperature sensor of the electronics member, a pressure sensor hole adapted to communicate with a return lumen and receive a pressure sensor of the electronics member, and a temperature sensor hole adapted to communicate with the return lumen and receive a temperature sensor of the electronics member.

A fourteenth aspect of the invention involves a method of using a single-use, disposable temperature and pressure sensor block member of a temperature and pressure sensor assembly of a circulation set for a heat transfer catheter. The method includes removably attaching a single-use, disposable temperature and pressure sensor block member of a temperature and pressure sensor assembly to a multi-use, non-disposable temperature and pressure sensor electronics member; coupling the single-use, disposable temperature and pressure sensor block member to the heat transfer catheter; circulating heat transfer fluid through the block member and heat transfer catheter; sensing temperature and pressure of heat transfer fluid flowing through the block member; and disposing the block member but not the electronics member after a single use of the heat transfer catheter.

A fifteenth aspect of the invention involves a method of using a single-use, disposable temperature and pressure sensor block member of a temperature and pressure sensor assembly of a circulation set for a heat transfer catheter. The method includes removably attaching a single-use, disposable temperature and pressure sensor block member of a temperature and pressure sensor assembly to a multi-use, non-disposable temperature and pressure sensor electronics member. The block member includes a supply lumen adapted to be coupled to the heat transfer catheter for delivery of heat transfer fluid thereto, a return lumen adapted to be coupled to the heat transfer catheter for delivery of heat transfer fluid therefrom, a pressure sensor hole adapted to communicate with the supply lumen and receive a sensor of the electronics member, a temperature sensor hole adapted to communicate with the supply lumen and receive a temperature sensor of the electronics member, a pressure sensor hole adapted to communicate with the return lumen and receive a pressure sensor of the electronics member, and a temperature sensor hole adapted to communicate with the return lumen and receive a temperature sensor of the electronics member; coupling the supply lumen and return lumen of the block member with the heat transfer catheter; circulating heat transfer fluid through the supply lumen of the block member, heat transfer catheter, and return lumen of the block member; sensing temperature and pressure of heat transfer fluid flowing through the supply lumen of the block member with the temperature and pressure sensors of the electronics member and sensing temperature and pressure of heat transfer fluid flowing through the return lumen of the block member with the temperature and pressure sensors of the electronics member; and disposing the block member but not the electronics member after a single use of the heat transfer catheter.

A sixteenth aspect of the invention involves a method of using a heat exchanger member in a circulation set for a heat transfer catheter, the circulation set including a heat exchanger adapted to transfer heat between the heat exchanger and heat transfer fluid within the heat exchanger member for temperature control of the heat transfer fluid. The method includes providing a single-use, disposable heat exchanger member with the heat exchanger, the heat exchanger member including at least one passage adapted to allow heat transfer fluid to flow therethrough; transferring heat between the heat exchanger and the heat transfer fluid in the heat exchanger member, either to the heat transfer fluid from the heat exchanger or from the heat transfer fluid to the heat exchanger; and disposing the heat exchanger member, but not the heat exchanger after a single use of the heat transfer catheter.

A seventeenth aspect of the invention involves a method of using a heat exchanger member in a circulation set for a heat transfer catheter, the circulation set including a heat exchanger adapted to transfer heat between the heat exchanger and heat transfer fluid within the heat exchanger member for temperature control of the heat transfer fluid. The method includes providing a single-use, disposable IV or intravenous bag normally used for the intravenous delivery of one or more fluids to the vasculature of a patient as a heat exchanger member with the heat exchanger, the IV bag including at least one passage adapted to allow heat transfer fluid to flow therethrough; transferring heat between the heat exchanger and the heat transfer fluid in the IV bag, either to the heat transfer fluid from the heat exchanger or from the heat transfer fluid to the heat exchanger; and disposing the IV bag but not the heat exchanger after a single use of the heat transfer catheter.

An eighteenth aspect of the invention involves a heat exchanger of a circulation set for a heat transfer catheter. The heat exchanger includes a pair of heat exchanger mold members each including an insulative body with an inner surface, a heat conductive face bonded to the inner surface of the face, and one or more heat transfer liquid paths located between the inner surface of the insulative body and the heat conductive face. The heat conductive face includes a mold configuration and is adapted, when placed together with the opposite face, to receive a disposable heat exchanger member and shape the disposable heat exchanger member into one or more heat transfer paths for transferring a heat transfer fluid therethrough.

A nineteenth aspect of the invention involves a method of identifying a heat transfer catheter or heat transfer element of a heat transfer catheter. The method includes measuring catheter pressure at a variety of heat transfer fluid flow rates; determining a slope of a best fit line through a variety of data points determined by the measuring step; and identifying the heat transfer catheter or heat transfer element by comparing the slope determined by the determining step to established slopes for a variety of different heat transfer catheters or heat transfer elements. In an implementation of the invention, the method further includes controlling one or more operational parameters of the catheter or heat transfer element based on the heat transfer catheter or heat transfer element identified.

The novel features of this invention, as well as the invention itself, will be best understood from the attached drawings, taken along with the following description, in which similar reference characters refer to similar parts, and in which:

BRIEF DESCRIPTION OF THE DRAWINGS

The drawings illustrate the design and utility of preferred embodiments of the present invention, in which:

FIG. 2 is a cross-sectional view of an embodiment of a distal portion of a heat transfer catheter along with a side-elevational view of an embodiment of a proximal portion of the catheter that may be used with the circulation set illustrated in FIG. 1;

DETAILED DESCRIPTION OF THE INVENTION

Figure 1:
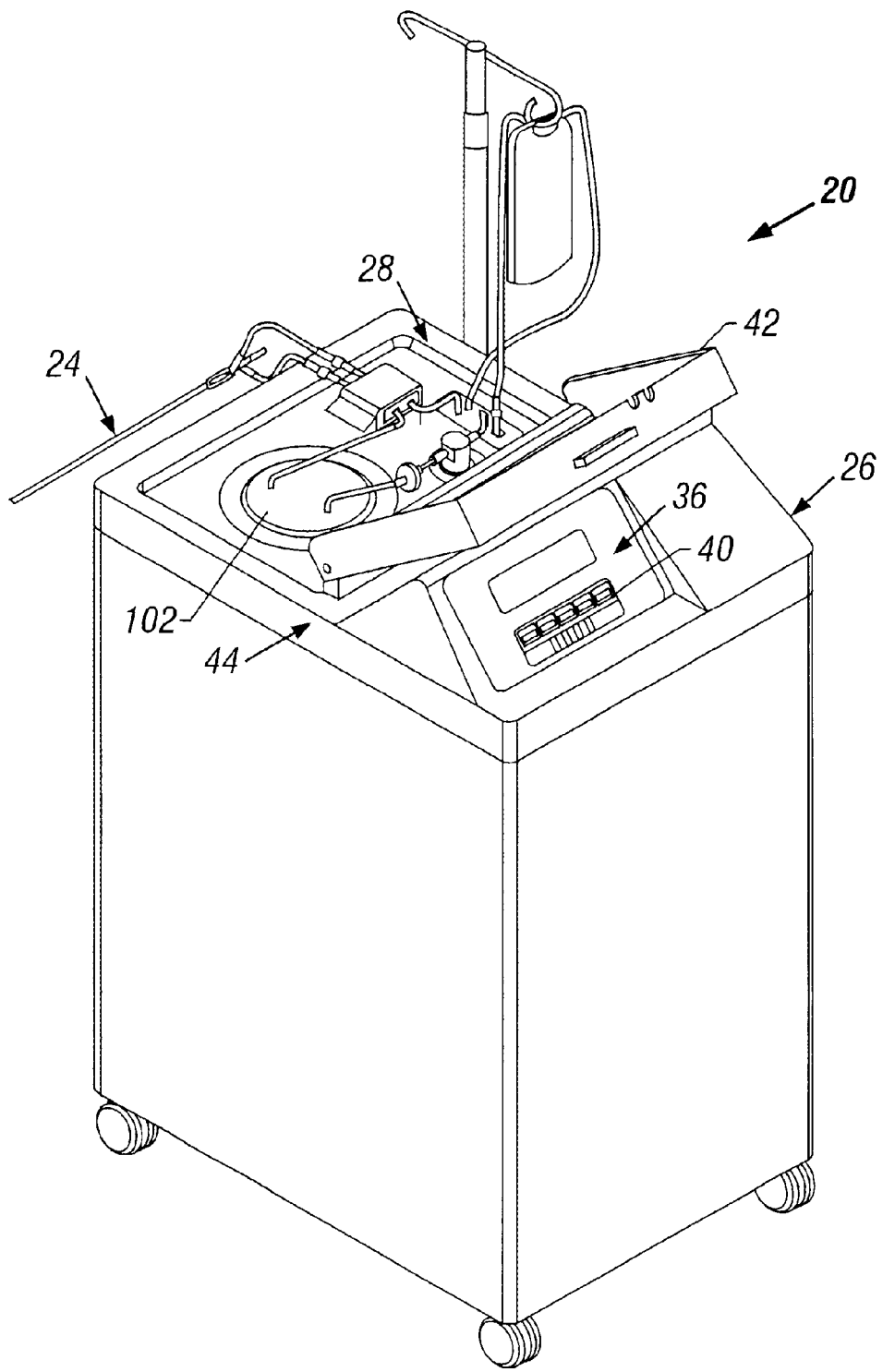
FIG. 1 is a perspective view of a heat transfer catheter system including a circulation set constructed in accordance with an embodiment of the invention.

With reference to FIG. 1, an embodiment of a heat transfer catheter system 20 includes a heat transfer catheter 24, a control system 26, and a circulation set 28 housed by the control unit system 26. The control system 26 may be equipped with an output display 36 and input keys 40 to facilitate user interaction with the control system 26. A hood 42 is pivotally connected to a control unit housing 44 for covering much of the circulation set 28.

With reference additionally to FIG. 2, in a preferred embodiment, the catheter 24 is a heat transfer catheter such as, but not by way of limitation, a hypothermia catheter capable of intravascular regulation of the temperature of a patient's body or one or more selected organs. The catheter 24 may include a heat transfer element 48 located at a distal portion thereof. In the embodiment of the heat transfer element shown, the heat transfer element 48 includes a supply lumen 50 and a return lumen 52. The supply lumen 50 and return lumen 52 preferably terminate at respective distal points in a distal portion of the heat transfer element 48 and terminate at respective proximal points at a supply lumen port 54 and a return lumen port 56 in catheter handle 58.

The heat transfer element 48 may be placed in the vasculature of the patient to absorb heat from or deliver heat to surrounding blood flowing along the heat transfer element 48, thereby regulating the temperature of a patient's body or one or more selected organs. In an analogous fashion, the heat transfer element 48 may be used within a volume of tissue to regulate the tissue temperature by absorbing heat from or delivering heat to a selected volume of tissue. In the latter case, heat transfer is predominantly by conduction.

In an exemplary application, the heat transfer catheter 24 may be used to cool the brain. One or more other organs, as well as the whole body, may also be cooled and/or heated, i.e., temperature controlled. The common carotid artery supplies blood to the head and brain. The internal carotid artery branches off the common carotid artery to supply blood to the anterior cerebrum. The heat transfer element 48 may be placed into the common carotid artery or into both the common carotid artery and the internal carotid artery via the femoral artery or other well known vascular routes. Heat transfer fluid supplied, chilled, and circulated by the circulation set 28 causes the heat transfer element 48 to draw heat from the surrounding blood flow in the carotid artery or internal carotid artery, causing cooling of the brain to, for example, reduce the effects of certain body injuries to the brain.

Although the catheter 24 has been described as including a specific heat transfer element 48, it will be readily apparent to those skilled in the art that the circulation set of the present invention may be used with heat transfer catheters including heat transfer elements other than the specific heat transfer element 48 described above. Further, although the circulation set 28 is described in conjunction with a heat transfer catheter, it will be readily apparent to those skilled in the art that the circulation set of the present invention may be used in conjunction with catheters other than hypothermia or heat transfer catheters. For example, the circulation set may be used with catheters that require a fluid to be supplied to and/or circulated through the catheter.

Circulation Set

Figure 3:
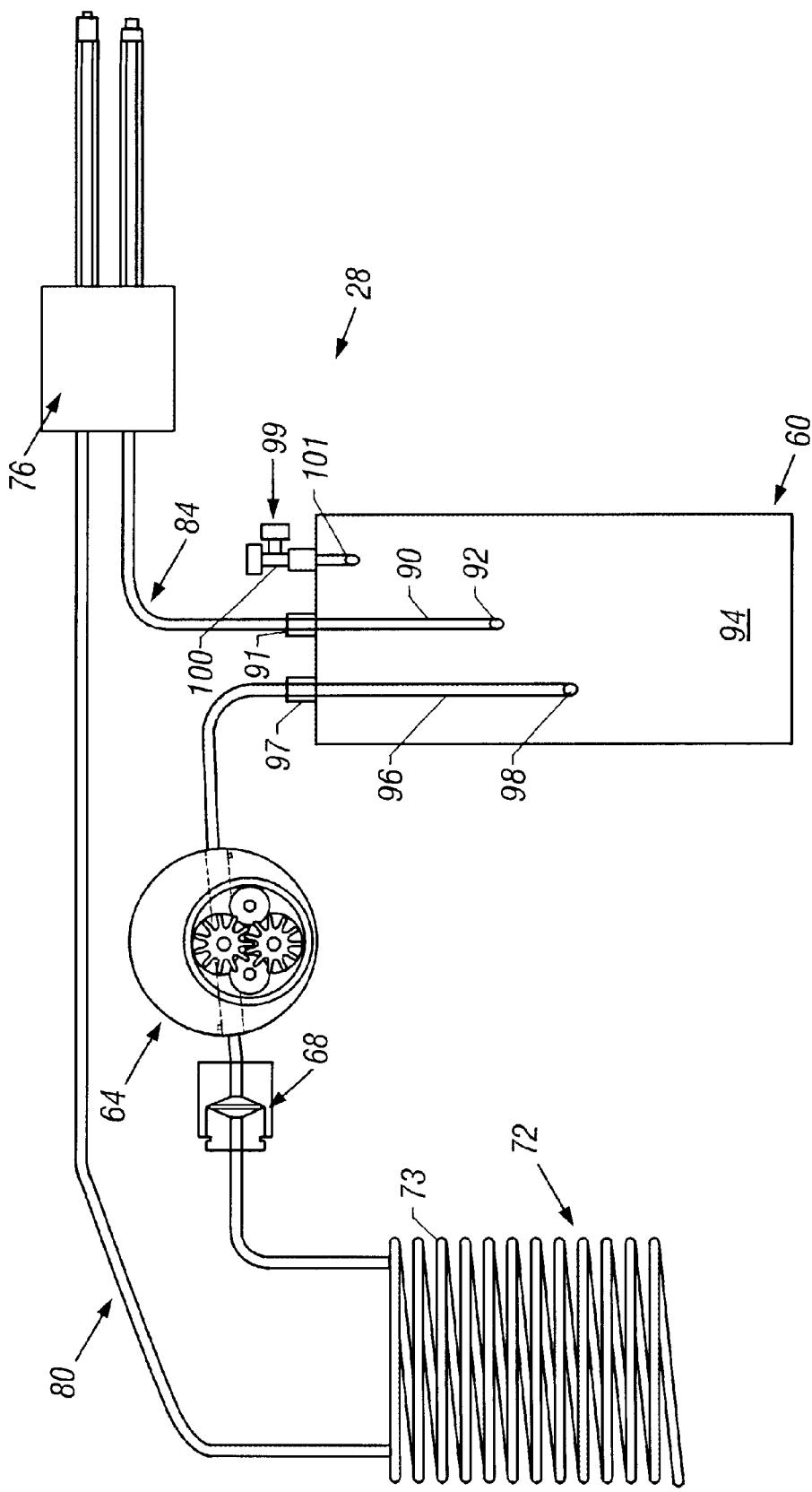
FIG. 3 is a schematic diagram of the circulation set illustrated in FIG. 1.

With reference to FIGS. 1 and 3, an embodiment of the circulation set 28 will now be described. The circulation set 28 may include one or more of the following: a fluid reservoir 60, a pump 64, a filter 68, a heat exchanger 72, a temperature and pressure sensor assembly 76, a supply line 80, and a return line 84. The supply lumen port 54 and return lumen portion are coupled with respective supply lines 80 and return lines 84 of the circulation set 28. The supply line 80 and return line 84 are preferably comprised of one or more pieces of tubing, connectors, etc. for joining the aforementioned components of the circulation set 28 to the supply lumen port 54 and return lumen port 56. The circulation set 28 may supply, filter, circulate, and/or be used to monitor the temperature and pressure of the heat transfer fluid for the catheter 24. Each of these components will now be described in turn.

Fluid Reservoir

In a preferred embodiment, the fluid reservoir 60 is a modified 250 ml IV bag made of PVC. The fluid reservoir 60 may be filled with a working fluid such as, but not by way of limitation, saline, freon, or perflourocarbon. In order to prevent the working fluid from causing EMI interference with other electronic devices used in the operating room, the working fluid may be a non-ionic fluid such as, but not by way of limitation, D5W, D5W with 1.5% glycerine, Sorbitol-Mannitol, and Ringer's Solution.

The fluid reservoir 60 may be used to prime the lines 80, 84 and lumens 50, 52 of the system 20. The fluid reservoir 60 includes a supply or inlet tube 90 that communicates at an inlet 91 with the return line 84 and communicates at an opposite end or outlet 92 with an inside 94 of the reservoir 60. The fluid reservoir 60 also includes a return or outlet tube 96 that communicates at one end with the supply line 80 and communicates at an opposite end or inlet 98, with the inside 94 of the reservoir 60.

The fluid reservoir 60 preferably also includes a mechanism 99 for purging, venting or removing air from the system 20. The air purging mechanism is used to remove air from the lines 80, 84 and lumens 50, 52 of the system 20 and, in a preferred embodiment, includes a needleless polycarbonate valve 100 with a polycarbonate vented spike 101. The removal or purging of air from the system 20 is important for maximizing the pressure in the system 20, maximizing heat transfer at the heat transfer element 48, and preventing air from possibly entering the blood stream of the patient caused by a break or leak in the catheter 24. The outlet 92 of the supply tube 90 may be located closer to the air purging mechanism 99 than the inlet 98 of the return tube 96 or adjacent to the air purging mechanism 99 to inhibit air bubbles supplied by the supply tube 90 from directly entering the return tube 96 without the opportunity to be removed by the air purging mechanism 99. The purging cycle will be discussed in greater detail below.

In an alternative embodiment of the circulation set, the fluid reservoir 60 may supply or prime the system 20 without recirculation of working fluid therethrough. In this embodiment, the reservoir 60 may not include the supply tube 90 and the air removal mechanism 99. The air removal mechanism 99 may be located in the circulation set 28 outside of the fluid reservoir 60.

The pump 64 is may be a disposable, plastic micro-pump that is disposed of or discarded with the other disposable components of the circulation set 28 after a single use. The pump 64 is used to draw the heat transfer fluid from the fluid reservoir and circulate the fluid throughout the lines 80, 84 and lumens 50, 52. In an alternative embodiment, the pump may be a permanent, non-disposable pump.

Filter

The filter 68 is preferably a 5 micron filter carried by male and female housing members. The filter 68 removes impurities from the circulating heat transfer fluid. In other embodiments of the circulation set 28, the circulation set 28 may include more than one filter 68, the circulation set 28 may include no filters 68, or the filter 68 may be a part of one or more components of the circulation set 28.

Heat Exchanger

In the embodiment of the circulation set illustrated in FIGS. 1 and 3, the heat exchanger 72 is a stainless steel tubing 73 that sits in a bath 102 of a second heat transfer fluid made of a biocompatible fluid such as, but not limited to, galden or ethylene glycol. This is an example of a wet heat exchanger because the tubing 73 resides within a liquid heat transfer fluid. A second heat exchanger (not shown) located in the control unit housing 44 regulates the temperature of the bath 102 for controlling the temperature of the heat transfer fluid in the system 20. The heat exchanger 72 is a reusable, non-disposable, wet heat exchanger.

Figure 4:
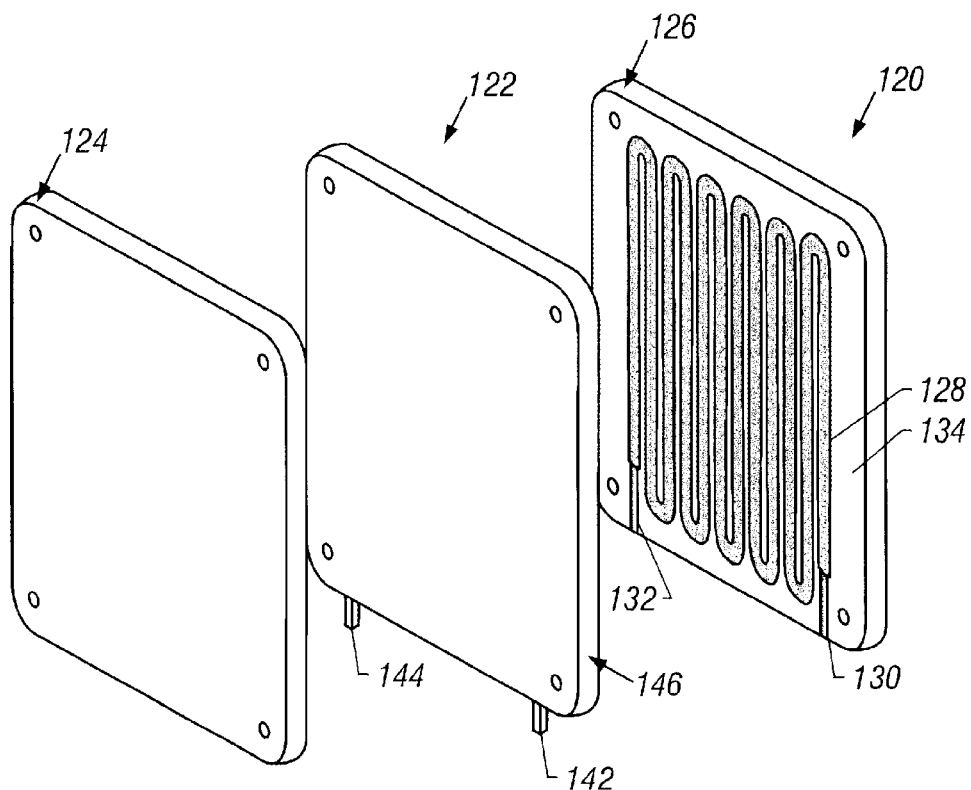
FIG. 4 is an exploded perspective view of an embodiment of a disposable heat exchanger that may be used in the circulation set of the present invention.
Figure 5:
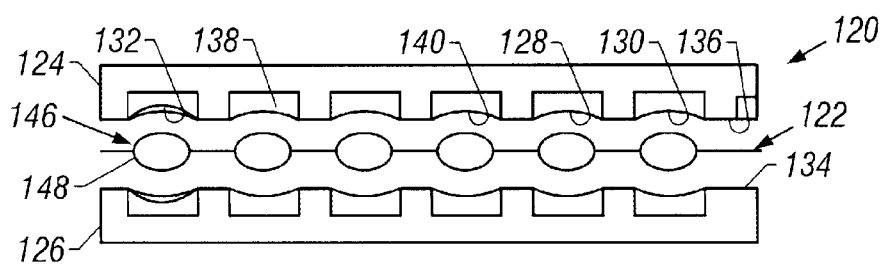
FIG. 5 is a cross sectional view of the heat exchanger illustrated in FIG. 4.
Figure 6A:
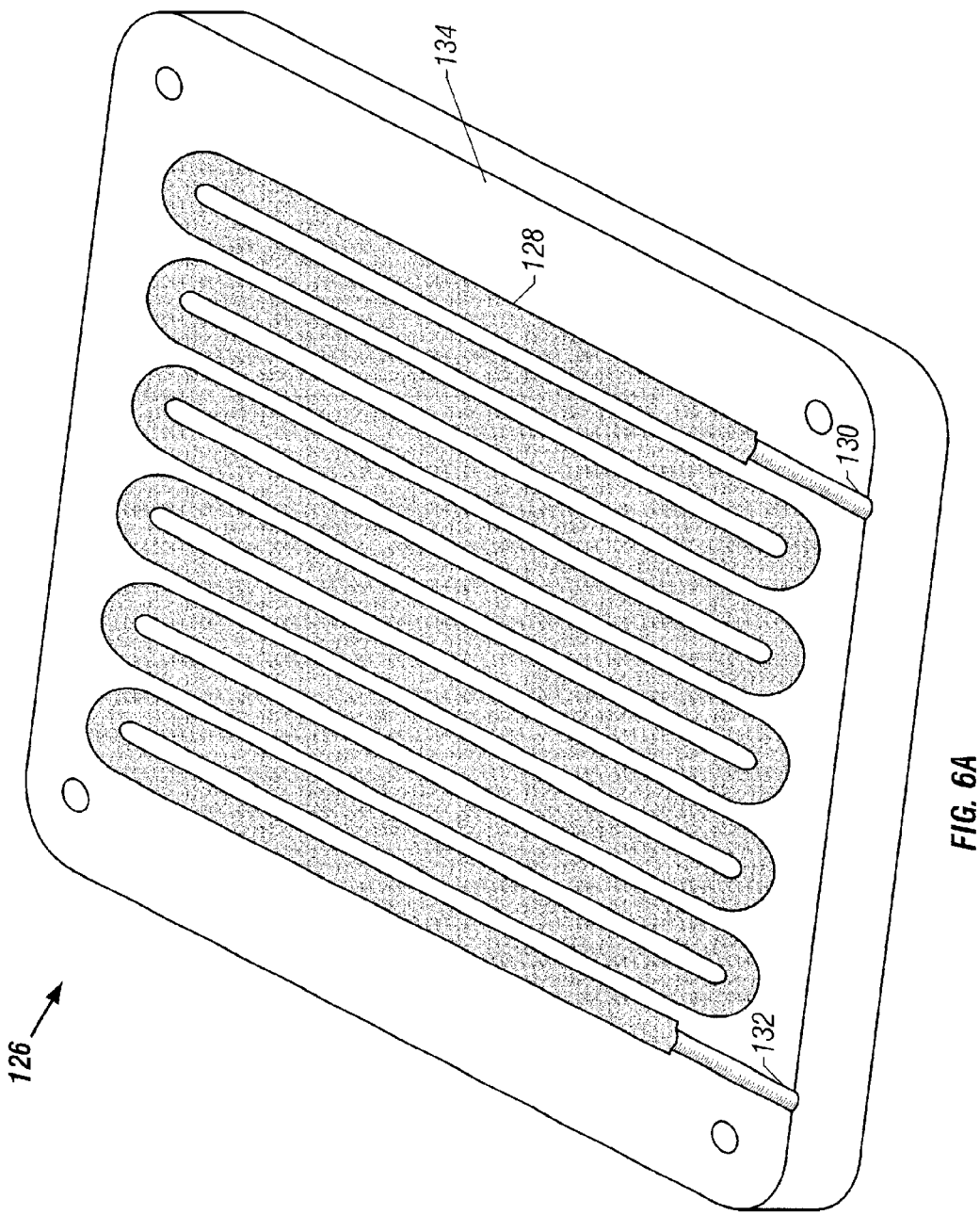
FIGS. 6A and 6B are perspective views of the manifold portions of the heat exchanger illustrated in FIG. 4.
Figure 6B:
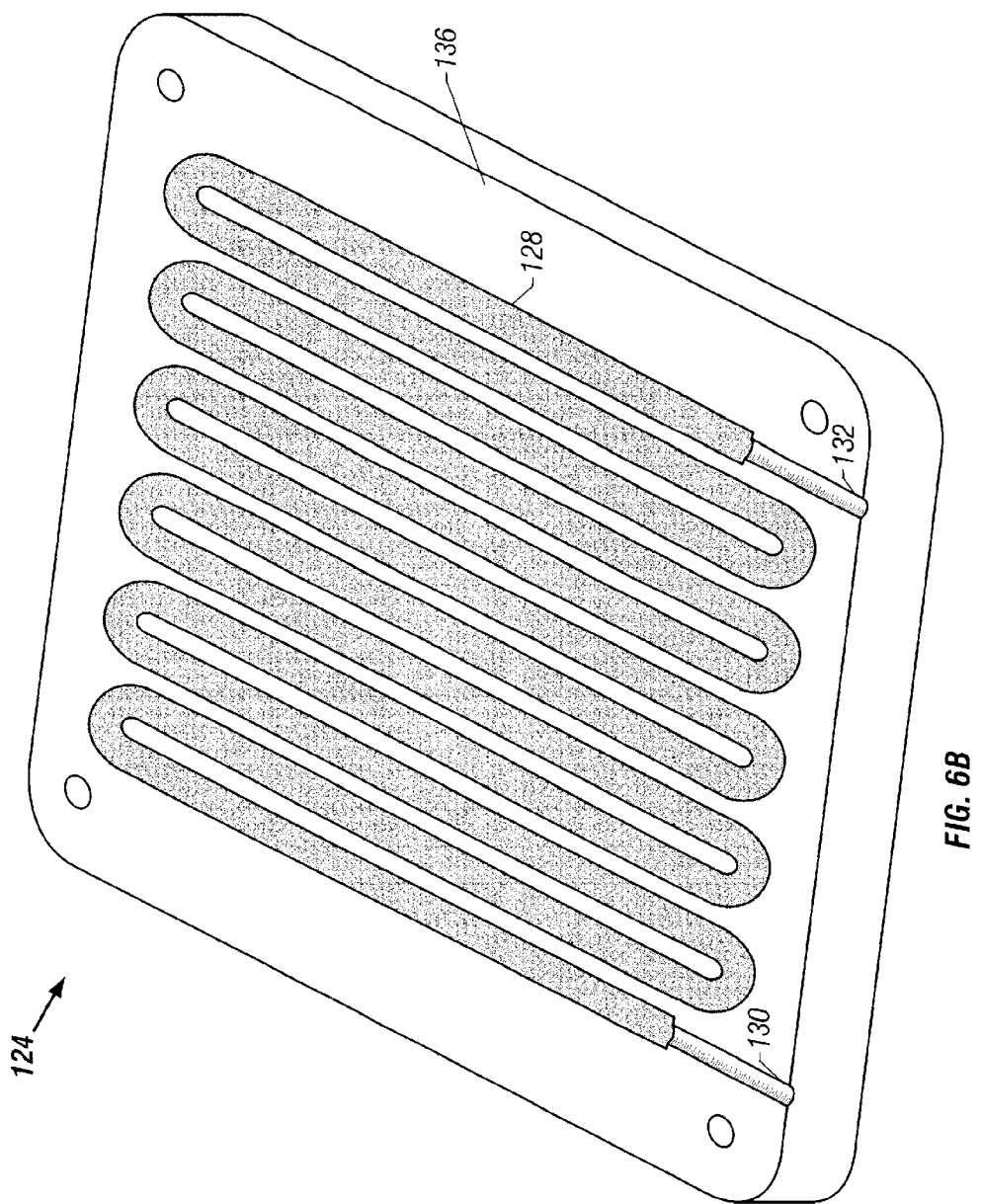

With reference to FIGS. 4–6, an embodiment of a dry heat exchanger 120 including a disposable, single-use heat exchanger member 122 may be used in the circulation set 28. The heat exchanger member 122 is removably securable within heat exchanger mold members 124, 126.

The heat exchanger mold members 124, 126 are preferably constructed of a thermoplastic insulative material and may include matching, mirrored serpentine grooves 128 therein. The serpentine grooves 128 terminate at one end in an inlet groove 130 and terminate at an opposite end in an outlet groove 132. The inlet groove 130 and outlet groove 132 accommodate inlet tube 142 and outlet tube 144 of the disposable heat exchanger member 222 and corresponding connection tubes (not shown) for connecting to the supply line 80. In an alternative embodiment, each heat exchanger mold member 124, 126 may have more than one inlet and/or outlet. Instead of serpentine grooves 128, each heat exchanger mold member may include one or more cavities that form reservoirs that heat transfer fluid flows through. First and second heat exchanger surfaces 134, 136 are located on inner faces of the mold members 124, 126. In a preferred embodiment, the heat exchanger surfaces 134, 136 are stamped stainless steel pieces of sheet metal that are bonded to the inner faces of the mold members 124, 126 so as to form heat transfer paths 138 (FIG. 5) therebetween. The heat exchanger surfaces 134, 136 preferably have serpentine grooves 140 stamped therein. In an alternative embodiment of the invention, each groove 140 may have a shape that is other than serpentine or there may be more or less channels in each serpentine groove 140. The heat exchanger surfaces 134, 136 isolate the disposable heat exchanger member 122 from the heat transfer fluid flowing through the heat transfer paths 138, making the heat exchanger a "dry" heat exchanger in that the heat transfer fluid, e.g., ethylene glycol, does not contact the external surface of the disposable heat exchanger member 126.

The disposable heat exchanger member 122 is preferably constructed of an IV bag and may include the aforementioned inlet tube 142 and outlet tube 144 welded to a bag body 146.

In use, the heat exchanger 120 is opened by separating the first heat exchanger mold member 124 and the second heat exchanger mold member 126, the disposable heat exchanger member 122 is placed therebetween, and the heat exchanger 120 is closed by bringing the first heat exchanger mold member 124 and the second heat exchanger mold member 126 together. When the heat exchanger 120 is closed, the disposable heat exchanger member 122 conforms to the shape of the serpentine grooves 140, forming corresponding serpentine fluid passages 148 in the disposable heat exchanger member 122. As working fluid flows through the serpentine passages 148, heat transferred between the heat transfer fluid in the heat transfer paths 138 and heat exchanger surfaces 134, 136 causes corresponding heat transfer between the heat exchanger surfaces 134, 136 and the working fluid in the serpentine passages 148. After use, the heat exchanger member 120 is opened by separating the first heat exchanger mold member 124 and the second heat exchanger mold member 126, and the disposable heat exchanger member 120 is disposed of with the rest of the disposable components of the circulation set 28.

Thus, the heat exchanger 120 is a dry heat exchanger because the external surface of the disposable heat exchanger member 120 does not contact a liquid, making it not as messy as the aforementioned coiled heat exchanger 72 that resides in a liquid bath. The heat exchanger member 122 is inexpensive and conveniently disposable after a single use.

In alternative embodiments of the invention, the heat exchanger may have a different construction. For example, a pair of heat exchangers 120 may be stacked on each other in a "double-decker" fashion, sharing a common heat exchanger mold member, the disposable heat exchanger member 120 may include a bag with serpentine or other-shaped passages already formed therein, or the disposable heat exchanger member 120 may be comprised of a stainless steal tube shaped in serpentine or other pattern.

Temperature and Pressure Sensor Assembly

With reference to FIGS. 7–10, the temperature and pressure sensor assembly 76 will now be described in more detail. The temperature and pressure sensor assembly 76 is used for measuring the temperature and the pressure of the heat transfer fluid in the supply line 80 before it enters the catheter 24, and measuring the temperature and the pressure of the heat transfer fluid in the return line 84, after it leaves the catheter 24. These measurements are important for determining the pressure of the heat transfer fluid flowing through the catheter 24 and the heat transfer that occurs at the heat transfer element 48 of the catheter 24. Heating or cooling efficiency of the heat transfer element 48 is optimized by maximizing the pressure or flow rate of working fluid through the catheter. Although the assembly 76 is described as a temperature and pressure assembly, the assembly 76 may be used to measure only temperature or pressure. Further, the assembly 76 may be used for measuring other physical characteristics of the working fluid.

The temperature and pressure sensor assembly 76 includes two main components, a multi-use, fixed, non-disposable temperature and pressure sensor electronics member 210 and a single-use, disposable temperature and pressure sensor block member 212.

Figure 7:
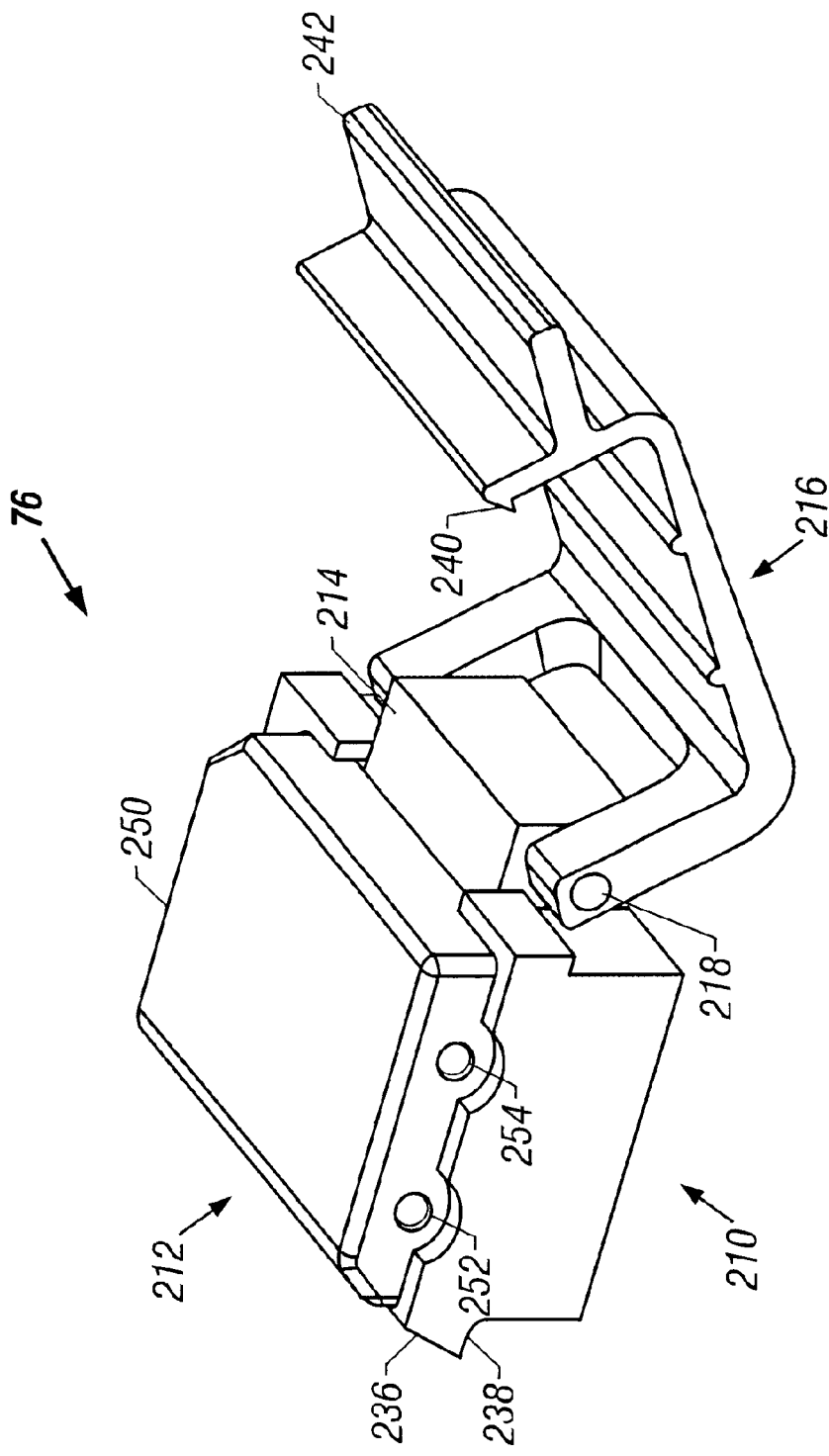
FIG. 7 is a perspective view of a temperature and pressure sensor assembly constructed in accordance with an embodiment of the invention.
Figure 8:
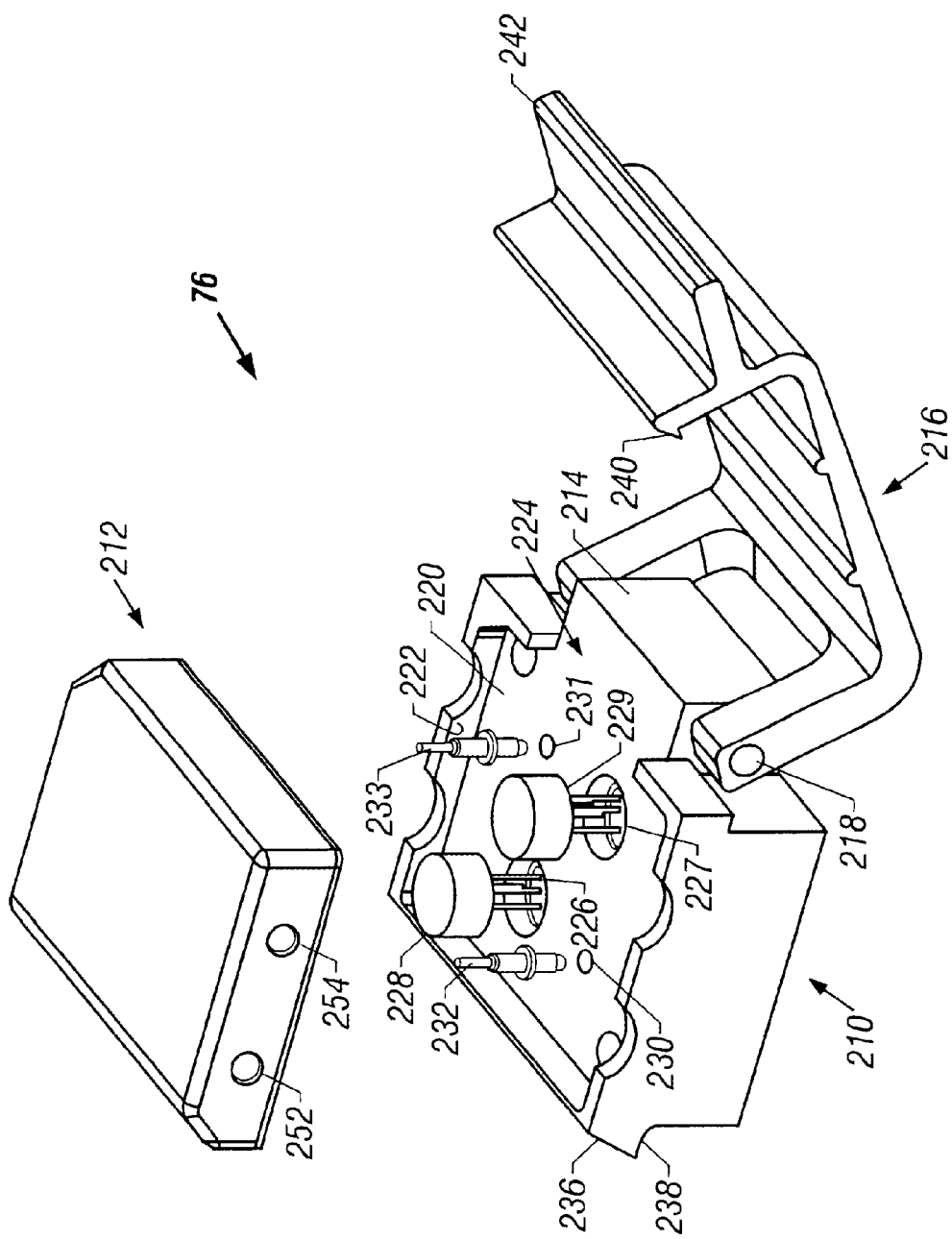
FIG. 8 is an exploded perspective view of the temperature and pressure sensor assembly illustrated in FIG. 7.

With reference to FIGS. 7–8, the temperature and pressure sensor electronics member 210 includes a base 214 and a latch 216 pivotally coupled thereto by a pin 218. The base 214 includes an upper surface 220 and a skirt 222 that together define a receiving area 224 for the temperature and pressure block member 212. The base 214 includes first and second round pressure transducer holes 226, 227 that receive corresponding first and second pressure transducers 228, 229 and first and second round thermocouple holes 230, 231 that receive corresponding first and second thermocouples 232, 233. The pressure transducers 228, 229 and thermocouples 232, 233 are coupled to electronic circuitry on an undersurface of the base 214. The electronic circuitry is coupled to the control system 26 via appropriate wiring. The base 214 includes a sloped surface 236 that terminates in a shoulder portion 238. The latch 216 includes a corresponding catch portion 240 that is biased outward and engages the shoulder portion 238 when the latch 216 is pivoted onto the base 214. The latch 216 also includes a protruding release member 242 that may be manipulated by a user's fingers to disengage the catch portion 240 of the latch 216 from the shoulder portion 238 of the base 214.

Figure 10:
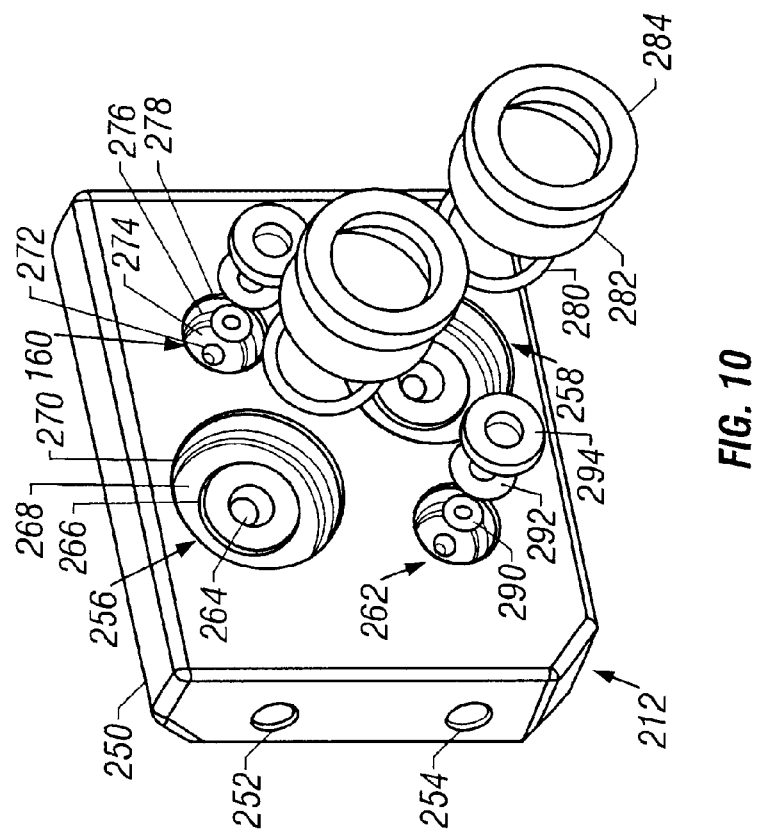
FIG. 10 is an exploded perspective view of the temperature and pressure sensor assembly illustrated in FIG. 7, but from a different vantage point from that of FIG. 8.
Figure 9:
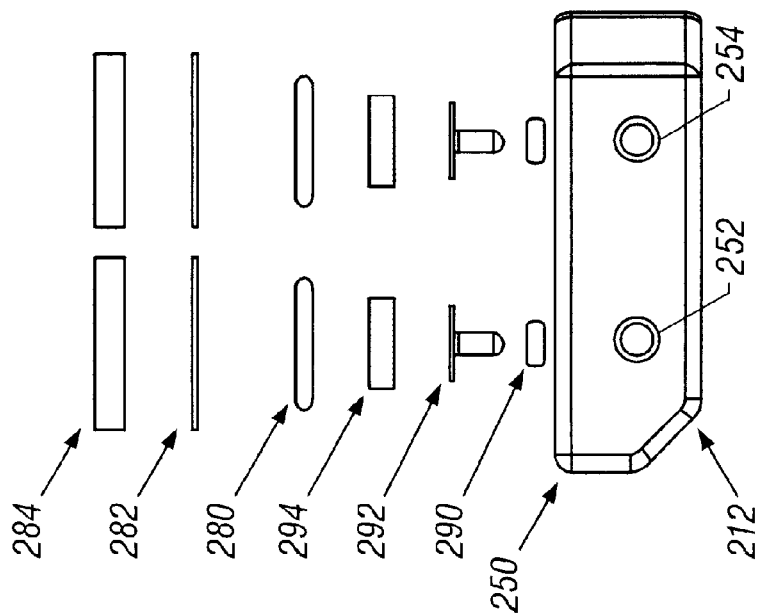
FIG. 9 is an exploded side-elevational view of the temperature and pressure sensor assembly illustrated in FIG. 7.

With reference to FIGS. 9 and 10, the disposable temperature and pressure sensor block member 212 includes a polycarbonate block or base 250 having first and second longitudinally extending lumens or tubes 252, 254 extending therethrough. The longitudinally extending lumens 252, 254 communicate with corresponding first and second pressure transducer wells 256, 258 (FIG. 9) and first and second thermocouple wells 260, 262. The pressure transducer wells 256, 258 include central holes 264 that communicate the respective longitudinally extending lumens 252, 254, an inner annular raised portion 266, an outer annular recessed portion 268, and an annular wall 270. The thermocouple wells 260, 262 include central holes 272 that communicate with the respective longitudinally extending lumens 252, 254, an inner annular recessed portion 274, an outer annular raised portion 276, and an annular wall 278.

Each pressure transducer well 256, 258 includes an O-Ring seal 280 fixed on the outer annular recessed portion 268, a pressure sensor diaphragm 282 fixed on the O-Ring seal 280, over the inner annular raised portion 266, and a pressure sensor bushing 284 fixed to the annular wall 270, over the diaphragm 282. Each thermocouple well 260, 262 includes an O-Ring seal 290 fixed on the inner annular recessed portion 274, a sensor connection tube 292 fixed on the O-Ring seal 290 and extending into the central hole 272, and a temperature sensor bushing 294 fixed to the annular wall 278, over the sensor connection tube 292.

The temperature and pressure sensor assembly 76 is assembled by fitting the temperature and pressure block member 212 onto the temperature and pressure electronics member 210 so that the pressure transducers 228, 229 and thermocouples 232, 233 of the electronics member 210 mate with the corresponding pressure transducer wells 256, 258 and thermocouple wells 260, 262 of the block member 212. The latch 216 is then pivoted to the locked or engaged position so that the catch portion 240 of the latch 216 engages the shoulder portion 238 of the base 214. This locks the block member 212 to the electronics member 210.

After a single use of the circulation set 28 or operation using the circulation set 28, the block member 212 is preferably removed from the electronics member 210 and disposed of. This is accomplished by disengaging the catch portion 240 of the latch 216 from the shoulder portion 238 of the base 214 by pulling on the release member 242. The block member 212 along with the other disposable components of the circulation set 28 are then disposed of. Thus, the only reusable component of the pressure and temperature assembly 76 is the temperature and pressure electronics member 210. The above-described construction and configuration of the block member 212 allows for its inexpensive manufacture, and thus, disposability, and the reusability of the electronics member 210 without contaminating any elements of the electronics member 210.

As discussed infra, the air purging mechanism 99 is used to remove air from the lines 80, 84 and lumens 50, 52 of the system 20. Removing air from the system 20 maximizes the pressure in the system 20, maximizes heat transfer at the heat transfer element 48, and reduces the risk of air entering the blood stream of the patient. The air purging mechanism 99 is employed during a purge phase before each use of the system 20. The purge phase is important for identification of the type of catheter being used and for early detection of problems with the system 20.

Figure 11:
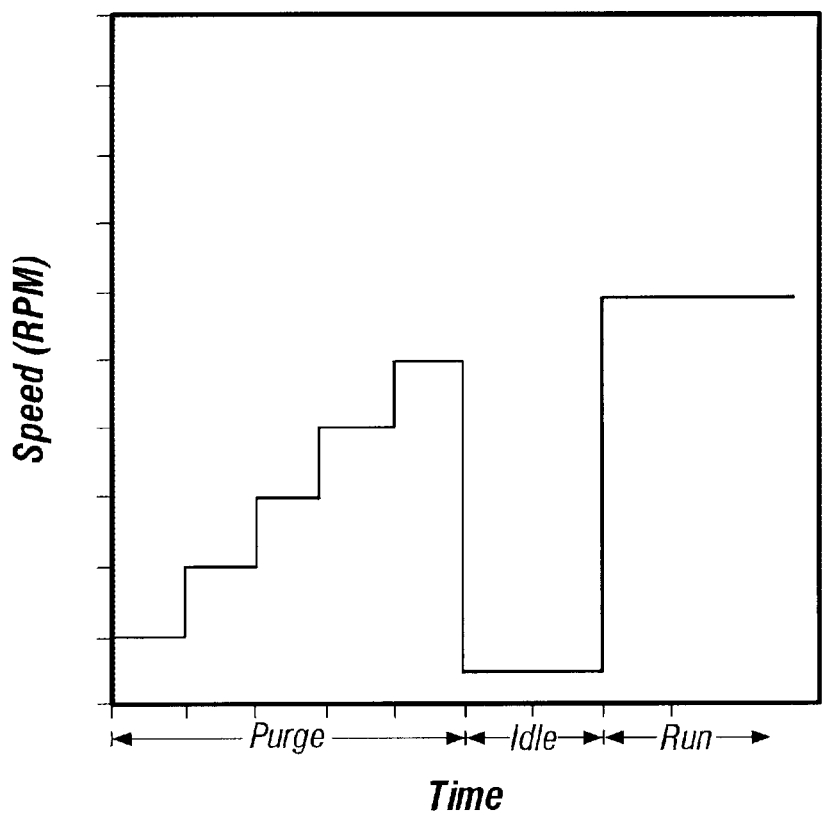
FIG. 11 is an exemplary graph of a pump motor speed versus time for a pump of the circulation set illustrated in FIG. 1.
Figure 12:
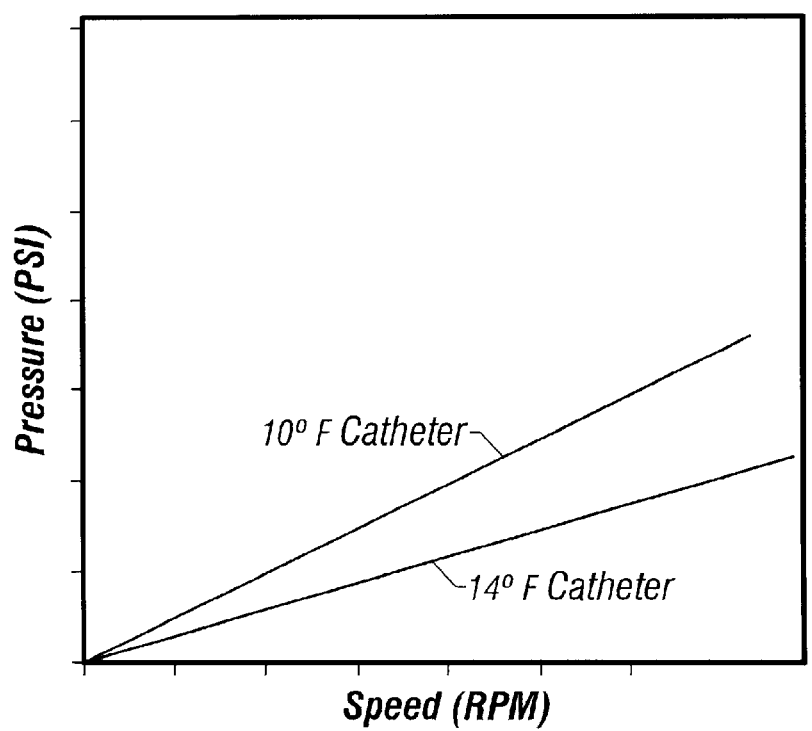
FIG. 12 is an exemplary graph of pressure versus pump motor speed for a 10 F heat transfer catheter and a 14 F heat transfer catheter used with the circulation set illustrated in FIG. 1.

With reference to FIGS. 11 and 12, a method of automatically identifying a catheter connected to the circulation set 28 or automatically identifying a heat transfer element attached to a catheter that is connected to a circulation set 28 based on a pressure reading in the circulation set 28 will now be described.

FIG. 11 is a graph generally illustrating pump motor speed versus time for exemplary purge, idle, and run cycles of the catheter system 20. The pump motor speed is representative of the fluid flow rate through the system 20. In the purge routine, the fluid flow rate is gradually increased in discrete steps.

With reference additionally to FIG. 12, each catheter 24 (e.g., 10 F, 14 F, etc.) or heat transfer element 48 connected to a catheter 24 has its own unique flow resistance, i.e., pressure versus flow response. If during each discrete step of the purge cycle, both the inlet pressure of the catheter 24 and the pump speed are measured, a straight line may be drawn through the measured data points and a slope computed. FIG. 12 illustrates such sloped lines for a 10 F catheter and a 14 F catheter attached to the circulation set 28. The catheter 24 or heat transfer element of a catheter 24 used with the circulation set 28 may be automatically identified by comparing the computed slope with a list of similarly computed slopes obtained empirically from a set of available catheters. After automatically identifying the catheter being used, the control system 26 may apply the corresponding optimal parameters for operation of the catheter 24. The computed slope may also be used to determine if a problem has occurred in the system 20, e.g., fluid leakage, if the computed slope does not match that of a specific reference catheter.

An exemplary practice of the present invention, for arterial applications, is illustrated in the following non-limiting example.

Exemplary Procedure

1. The patient is initially assessed, resuscitated, and stabilized.

2. The procedure is carried out in an angiography suite or surgical suite equipped with fluoroscopy.

3. Because the catheter is placed into the common carotid artery, it is important to determine the presence of stenotic atheromatous lesions. A carotid duplex (Doppler/ultrasound) scan can quickly and non-invasively make this determination. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities >100 cm/sec in the internal indicate the presence of at least 70% stenosis. Stenosis of 70% or more may warrant the placement of a stent to open up the internal artery diameter.

4. The ultrasound can also be used to determine the vessel diameter and the blood flow and the catheter with the appropriately sized heat transfer element are selected.

5. After assessment of the arteries, the patient's inguinal region is sterilely prepped and infiltrated with lidocaine.

6. The femoral artery is cannulated and a guide wire may be inserted to the desired carotid artery. Placement of the guide wire is confirmed with fluoroscopy.

7. An angiographic catheter can be fed over the wire and contrast media injected into the artery to further to assess the anatomy of the carotid.

8. Alternatively, the femoral artery is cannulated and a 10–12.5 french (f) introducer sheath is placed.

9. A guide catheter is placed into the desired common carotid artery. If a guiding catheter is placed, it can be used to deliver contrast media directly to further assess carotid anatomy.

10. A 10 f–12 f (3.3–4.0 mm) (approximate) cooling catheter is subsequently filled with saline and all air bubbles are removed.

11. The cooling catheter is placed into the carotid artery via the guiding catheter or over the guidewire. Placement is confirmed with fluoroscopy.

12. The cooling catheter is connected to the aforementioned circulation set. An ionic or non-ionic heat transfer fluid is supplied by the fluid reservoir or IV bag.

13. Cooling is initiated by starting the pump and the heat transfer fluid is circulated through the circulation set and catheter at 3–8 cc/sec. The heat transfer fluid travels through the circulation set and is cooled to approximately 1° C. The fluid travels through the heat exchanger and is simultaneously cooled. The air purge mechanism is used to remove air bubbles or pockets from the fluid lines. Priming and purging may also be done before the cooling catheter is introduced into the patient's body. As discussed above, the control system may automatically identify the type of catheter or heat transfer element on the catheter based on catheter inlet pressure readings made during the purge cycle. Once the identity of the catheter or heat transfer element on the catheter is known, the control system may then determine optimum operating parameters for the catheter/heat transfer element or if a problem exists.

14. The heat transfer fluid subsequently enters the cooling catheter where it is delivered to the heat transfer element. The heat transfer fluid is warmed to approximately 5–7° C. as it travels along the inner lumen of the catheter shaft to the end of the heat transfer element.

15. The heat transfer fluid then flows back through the heat transfer element in contact with the inner metallic surface. The heat transfer fluid is further warmed in the heat transfer element to 12–15° C., and in the process, heat is absorbed from the blood, cooling the blood to 30° C. to 32° C.

16. The chilled blood then goes on to chill the brain. It is estimated that 15–30 minutes will be required to cool the brain to 30 to 32° C.

17. The warmed heat transfer fluid travels back down the outer lumen of the catheter shaft and back through the circulation set where it is cooled to 1° C.

18. The pressure drops along the length of the circuit are estimated to be, e.g., 6 atmospheres.

19. The cooling can be adjusted by increasing or decreasing the flow rate of the heat transfer fluid, or by changing the temperature of the heat transfer fluid. The temperature and pressure of the heat transfer fluid entering the catheter and exiting the catheter is monitored with the temperature and pressure sensor assembly. Monitoring temperature and pressure at these points yield the temperature and pressure drop through the catheter. Monitoring the temperature and pressure drop of the heat transfer fluid through the catheter will allow the flow rate and cooling to be adjusted to maintain the desired cooling effect.

20. The catheter is left in place to provide cooling for up to or more than 12 to 24 hours.

21. If desired, warm heat transfer fluid can be circulated to promote warming of the brain at the end of the procedure.

22. After the procedure is completed, the supply line and return line are disconnected from the catheter, and the temperature and sensor block member is disconnected from the temperature and sensor electronics member. If the disposable heat exchanger member is used, the disposable heat exchanger member may be removed from the first and second heat exchanger mold members and disposed of along with the other disposable components of the circulation set.

The invention has been described with respect to certain embodiments. It will be clear to one of skill in the art that variations of the embodiments may be employed in the method of the invention. Accordingly, the invention is limited only by the scope of the appended claims.

What is claimed is:

1. A single-use, disposable circulation set for a heat transfer catheter, comprising:
    a single-use, disposable fluid reservoir adapted to supply a heat transfer fluid to the catheter;
    a single-use, disposable pump adapted to pump heat transfer fluid through said catheter from said fluid reservoir;
    a single-use, disposable filter assembly adapted to remove impurities from said heat transfer fluid;
    a single-use, disposable heat exchanger member adapted for use with a heat exchanger for transferring heat between said heat exchanger and said fluid;
    a single-use, disposable temperature and pressure sensor block member for use with a multi-use, non-disposable temperature and pressure sensor electronics member;
    a single-use, disposable supply line communicating said fluid reservoir, pump, filter assembly, heat exchanger, and temperature and pressure sensor block member, and adapted to be connected to said catheter for supplying heat transfer fluid to said catheter; and
    a single-use, disposable return line communicating said temperature and pressure sensor block member and fluid reservoir, and adapted to be connected to said catheter for returning heat transfer fluid to said fluid reservoir,
        wherein said single-use, disposable temperature and pressure sensor block member includes a supply lumen in communication with said supply line and a return lumen in communication with said return line.

2. The circulation set of claim 1, wherein said single-use, disposable temperature and pressure sensor block member includes a pressure sensor hole in communication with said supply lumen and adapted to receive a pressure sensor of said electronics member, a temperature sensor hole in communication with said supply lumen and adapted to receive a temperature sensor of said electronics member, a pressure sensor hole in communication with said return lumen and adapted to receive a pressure sensor of said electronics member, and a temperature sensor hole in communication with said return lumen and adapted to receive a temperature sensor of said electronics member.

3. The circulation set of claim 2, further including a single-use, disposable temperature sensor coupler adapted to be received by said temperature sensor and communicate with said heat transfer fluid via said temperature sensor hole, said coupler made of a material having a high thermal conductivity so that said temperature sensor accurately senses the temperature of said heat transfer fluid without contacting said heat transfer fluid.

4. The circulation set of claim 2, further including a single-use, disposable pressure sensor membrane disposed in said pressure sensor hole and adapted to be operatively associated with said pressure sensor and communicate with said heat transfer fluid to sense the pressure of said heat transfer fluid without contacting it.

5. A single-use, disposable circulation set for a heat transfer catheter, comprising:
    a single-use, disposable fluid reservoir adapted to supply a heat transfer fluid to the catheter;
    a single-use, disposable pump adapted to pump heat transfer fluid through said catheter from said fluid reservoir;
    a single-use, disposable filter assembly adapted to remove impurities from said heat transfer fluid;
    a single-use, disposable heat exchanger member adapted for use with a heat exchanger for transferring heat between said heat exchanger and said fluid;
    a single-use, disposable temperature and pressure sensor block member for use with a multi-use, non-disposable temperature and pressure sensor electronics member;
    a single-use, disposable supply line communicating said fluid reservoir, pump, filter assembly, heat exchanger, and temperature and pressure sensor block member, and adapted to be connected to said catheter for supplying heat transfer fluid to said catheter; and
    a single-use, disposable return line communicating said temperature and pressure sensor block member and fluid reservoir, and adapted to be connected to said catheter for returning heat transfer fluid to said fluid reservoir,
        wherein said fluid reservoir is an IV bag.

6. A single-use, disposable circulation set for a heat transfer catheter, comprising:
    a single-use, disposable fluid reservoir adapted to supply a heat transfer fluid to the catheter;
    a single-use, disposable pump adapted to pump heat transfer fluid through said catheter from said fluid reservoir;
    a single-use, disposable filter assembly adapted to remove impurities from said heat transfer fluid;
    a single-use, disposable heat exchanger member adapted for use with a heat exchanger for transferring heat between said heat exchanger and said fluid;
    a single-use, disposable temperature and pressure sensor block member for use with a multi-use, non-disposable temperature and pressure sensor electronics member;
    a single-use, disposable supply line communicating said fluid reservoir, pump, filter assembly, heat exchanger, and temperature and pressure sensor block member, and adapted to be connected to said catheter for supplying heat transfer fluid to said catheter; and
    a single-use, disposable return line communicating said temperature and pressure sensor block member and fluid reservoir, and adapted to be connected to said catheter for returning heat transfer fluid to said fluid reservoir,
        wherein said circulation set includes an air-removal mechanism.

7. The circulation set of claim 6, wherein said fluid reservoir includes the air-removal mechanism.

8. The circulation set of claim 7, wherein said return line terminates at an outlet inside said fluid reservoir and said supply line terminates at an inlet inside said fluid reservoir.

9. The circulation set of claim 8, wherein said outlet of said return line is located closer to said air-removal mechanism than the inlet of said supply line.

10. The circulation set of claim 9, wherein said outlet of said return line is located adjacent to said air-removal mechanism.

11. A single-use, disposable circulation set for a heat transfer catheter, comprising:

a single-use, disposable fluid reservoir adapted to supply a heat transfer fluid to the catheter;

a single-use, disposable pump adapted to pump heat transfer fluid through said catheter from said fluid reservoir;

a single-use, disposable filter assembly adapted to remove impurities from said heat transfer fluid;

a single-use, disposable heat exchanger member adapted for use with a heat exchanger for transferring heat between said heat exchanger and said fluid;

a single-use, disposable temperature and pressure sensor block member for use with a multi-use, non-disposable temperature and pressure sensor electronics member;

a single-use, disposable supply line communicating said fluid reservoir, pump, filter assembly, heat exchanger, and temperature and pressure sensor block member, and adapted to be connected to said catheter for supplying heat transfer fluid to said catheter; and a single-use, disposable return line communicating said temperature and pressure sensor block member and fluid reservoir, and adapted to be connected to said catheter for returning heat transfer fluid to said fluid reservoir, wherein said heat exchanger member is an IV bag adapted to be removably disposed between a pair of heat exchanger molds.

12. The circulation set of claim 11, wherein said IV bag is adapted to be shaped into a serpentine heat transfer fluid path.

13. A method of using a circulation set for a heat transfer catheter, comprising:

providing a single-use, disposable circulation set for the catheter, comprising:

a single-use, disposable fluid reservoir adapted to supply a heat transfer fluid to the catheter;

a single-use, disposable pump adapted to pump heat transfer fluid through said catheter from said fluid reservoir;

a single-use, disposable filter assembly adapted to remove impurities from said heat transfer fluid;

a single-use, disposable heat exchanger member adapted for use with a multi-use, non-disposable heat exchanger for transferring heat between said heat exchanger and said fluid;

a single-use, disposable temperature and pressure sensor block member for use with a multi-use, non-disposable temperature and pressure sensor electronics member;

a single-use, disposable supply line communicating said fluid reservoir, pump, filter assembly, heat exchanger, and temperature and pressure sensor block member, and adapted to be connected to said catheter for supplying heat transfer fluid to said catheter; and a single-use, disposable return line communicating said temperature and pressure sensor block member and fluid reservoir, and adapted to be connected to said catheter for returning heat transfer fluid to said fluid reservoir;

connecting said return line and supply line to said catheter;

coupling said single-use, disposable temperature and pressure sensor block member with said multi-use, non-disposable temperature and pressure sensor electronics member;

coupling said single-use, disposable heat exchanger member with said multi-use, non-disposable heat exchanger;

circulating heat transfer fluid and controlling the flow rate and temperature of the same through said catheter with said pump, heat exchanger, and said temperature and pressure sensor block member and electronics member;

disposing said circulation set after a single use, wherein said single-use, disposable temperature and pressure sensor block member includes a block made of polycarbonate.

14. A method of using a circulation set for a heat transfer catheter, comprising:

providing a single-use, disposable circulation set for the catheter, comprising:

a single-use, disposable fluid reservoir adapted to supply a heat transfer fluid to the catheter;

a single-use, disposable pump adapted to pump heat transfer fluid through said catheter from said fluid reservoir;

a single-use, disposable filter assembly adapted to remove impurities from said heat transfer fluid;

a single-use, disposable heat exchanger member adapted for use with a multi-use, non-disposable heat exchanger for transferring heat between said heat exchanger and said fluid;

a single-use, disposable temperature and pressure sensor block member for use with a multi-use, non-disposable temperature and pressure sensor electronics member;

a single-use, disposable supply line communicating said fluid reservoir, pump, filter assembly, heat exchanger, and temperature and pressure sensor block member, and adapted to be connected to said catheter for supplying heat transfer fluid to said catheter; and a single-use, disposable return line communicating said temperature and pressure sensor block member and fluid reservoir, and adapted to be connected to said catheter for returning heat transfer fluid to said fluid reservoir;

connecting said return line and supply line to said catheter;

coupling said single-use, disposable temperature and pressure sensor block member with said multi-use, non-disposable temperature and pressure sensor electronics member;

coupling said single-use, disposable heat exchanger member with said multi-use, non-disposable heat exchanger;

circulating heat transfer fluid and controlling the flow rate and temperature of the same through said catheter with said pump, heat exchanger, and said temperature and pressure sensor block member and electronics member;

disposing said circulation set after a single use, wherein said single-use, disposable temperature and pressure sensor block member includes a supply lumen in communication with said supply line and a return lumen in communication with said return line.

15. The method of claim 14, wherein said single-use, disposable temperature and pressure sensor block member includes a pressure sensor hole in communication with said supply lumen and adapted to receive a pressure sensor of said electronics member, a temperature sensor hole in communication with said supply lumen and adapted to receive a temperature sensor of said electronics member, a pressure sensor hole in communication with said return lumen and adapted to receive a pressure sensor of said electronics member, and a temperature sensor hole in communication with said return lumen and adapted to receive a temperature sensor of said electronics member.

16. The method of claim 15, further including a single-use, disposable temperature sensor coupler adapted to be received by said temperature sensor and communicate with said heat transfer fluid via said temperature sensor hole, said coupler made of a material having a high thermal conductivity so that said temperature sensor accurately senses the temperature of said heat transfer fluid without contacting said heat transfer fluid.

17. The method of claim 15, further including a single-use, disposable pressure sensor membrane disposed in said pressure sensor hole and adapted to be operatively associated with said pressure sensor and communicate with said heat transfer fluid to sense the pressure of said heat transfer fluid without contacting it.

18. A method of using a circulation set for a heat transfer catheter, comprising:
   providing a single-use, disposable circulation set for the catheter, comprising:
      a single-use, disposable fluid reservoir adapted to supply a heat transfer fluid to the catheter;
      a single-use, disposable pump adapted to pump heat transfer fluid through said catheter from said fluid reservoir;
      a single-use, disposable filter assembly adapted to remove impurities from said heat transfer fluid;
      a single-use, disposable heat exchanger member adapted for use with a multi-use, non-disposable heat exchanger for transferring heat between said heat exchanger and said fluid;
      a single-use, disposable temperature and pressure sensor block member for use with a multi-use, non-disposable temperature and pressure sensor electronics member;
      a single-use, disposable supply line communicating said fluid reservoir, pump, filter assembly, heat exchanger, and temperature and pressure sensor block member, and adapted to be connected to said catheter for supplying heat transfer fluid to said catheter; and
      a single-use, disposable return line communicating said temperature and pressure sensor block member and fluid reservoir, and adapted to be connected to said catheter for returning heat transfer fluid to said fluid reservoir;
   connecting said return line and supply line to said catheter;
   coupling said single-use, disposable temperature and pressure sensor block member with said multi-use, non-disposable temperature and pressure sensor electronics member;
   coupling said single-use, disposable heat exchanger member with said multi-use, non-disposable heat exchanger;
   circulating heat transfer fluid and controlling the flow rate and temperature of the same through said catheter with said pump, heat exchanger, and said temperature and pressure sensor block member and electronics member;
   disposing said circulation set after a single use,
   wherein said fluid reservoir is an IV bag.

19. A method of using a circulation set for a heat transfer catheter, comprising:
   providing a single-use, disposable circulation set for the catheter, comprising:
      a single-use, disposable fluid reservoir adapted to supply a heat transfer fluid to the catheter;
      a single-use, disposable pump adapted to pump heat transfer fluid through said catheter from said fluid reservoir;
      a single-use, disposable filter assembly adapted to remove impurities from said heat transfer fluid;
      a single-use, disposable heat exchanger member adapted for use with a multi-use, non-disposable heat exchanger for transferring heat between said heat exchanger and said fluid;
      a single-use, disposable temperature and pressure sensor block member for use with a multi-use, non-disposable temperature and pressure sensor electronics member;
      a single-use, disposable supply line communicating said fluid reservoir, pump, filter assembly, heat exchanger, and temperature and pressure sensor block member, and adapted to be connected to said catheter for supplying heat transfer fluid to said catheter; and
      a single-use, disposable return line communicating said temperature and pressure sensor block member and fluid reservoir, and adapted to be connected to said catheter for returning heat transfer fluid to said fluid reservoir;
   connecting said return line and supply line to said catheter;
   coupling said single-use, disposable temperature and pressure sensor block member with said multi-use, non-disposable temperature and pressure sensor electronics member;
   coupling said single-use, disposable heat exchanger member with said multi-use, non-disposable heat exchanger;
   circulating heat transfer fluid and controlling the flow rate and temperature of the same through said catheter with said pump, heat exchanger, and said temperature and pressure sensor block member and electronics member;
   disposing said circulation set after a single use,
   wherein said circulation set includes an air-removal mechanism.

20. A method of using a circulation set for a heat transfer catheter, comprising:
   providing a single-use, disposable circulation set for the catheter, comprising:
      a single-use, disposable fluid reservoir adapted to supply a heat transfer fluid to the catheter;
      a single-use, disposable pump adapted to pump heat transfer fluid through said catheter from said fluid reservoir;
      a single-use, disposable filter assembly adapted to remove impurities from said heat transfer fluid;
      a single-use, disposable heat exchanger member adapted for use with a multi-use, non-disposable heat exchanger for transferring heat between said heat exchanger and said fluid;
      a single-use, disposable temperature and pressure sensor block member for use with a multi-use, non-disposable temperature and pressure sensor electronics member;
      a single-use, disposable supply line communicating said fluid reservoir, pump, filter assembly, heat exchanger, and temperature and pressure sensor block member, and adapted to be connected to said catheter for supplying heat transfer fluid to said catheter; and
      a single-use, disposable return line communicating said temperature and pressure sensor block member and fluid reservoir, and adapted to be connected to said catheter for returning heat transfer fluid to said fluid reservoir;

connecting said return line and supply line to said catheter;

coupling said single-use, disposable temperature and pressure sensor block member with said multi-use, non-disposable temperature and pressure sensor electronics member;

coupling said single-use, disposable heat exchanger member with said multi-use, non-disposable heat exchanger;

circulating heat transfer fluid and controlling the flow rate and temperature of the same through said catheter with said pump, heat exchanger, and said temperature and pressure sensor block member and electronics member;

disposing said circulation set after a single use, wherein said fluid reservoir includes an air-removal mechanism.

21. The method of claim 20, wherein said return line terminates at an outlet inside said fluid reservoir and said supply line terminates at an inlet inside said fluid reservoir.

22. The method of claim 21, wherein said outlet of said return line is located closer to said air-removal mechanism than the inlet of said supply line.

23. The method of claim 22, wherein said outlet of said return line is located adjacent to said air-removal mechanism.

24. A method of using a circulation set for a heat transfer catheter, comprising:

providing a single-use, disposable circulation set for the catheter, comprising:
　a single-use, disposable fluid reservoir adapted to supply a heat transfer fluid to the catheter;
　a single-use, disposable pump adapted to pump heat transfer fluid through said catheter from said fluid reservoir;
　a single-use, disposable filter assembly adapted to remove impurities from said heat transfer fluid;
　a single-use, disposable heat exchanger member adapted for use with a multi-use, non-disposable heat exchanger for transferring heat between said heat exchanger and said fluid;
　a single-use, disposable temperature and pressure sensor block member for use with a multi-use, non-disposable temperature and pressure sensor electronics member;
　a single-use, disposable supply line communicating said fluid reservoir, pump, filter assembly, heat exchanger, and temperature and pressure sensor block member, and adapted to be connected to said catheter for supplying heat transfer fluid to said catheter; and
　a single-use, disposable return line communicating said temperature and pressure sensor block member and fluid reservoir, and adapted to be connected to said catheter for returning heat transfer fluid to said fluid reservoir;

connecting said return line and supply line to said catheter;

coupling said single-use, disposable temperature and pressure sensor block member with said multi-use, non-disposable temperature and pressure sensor electronics member;

coupling said single-use, disposable heat exchanger member with said multi-use, non-disposable heat exchanger;

circulating heat transfer fluid and controlling the flow rate and temperature of the same through said catheter with said pump, heat exchanger, and said temperature and pressure sensor block member and electronics member;

disposing said circulation set after a single use, wherein said heat exchanger member is adapted to be used with a dry heat exchanger so that an outer surface of said heat exchanger member does not contact a heat transfer liquid.

25. A method of using a circulation set for a heat transfer catheter, comprising:

providing a single-use, disposable circulation set for the catheter, comprising:
　a single-use, disposable fluid reservoir adapted to supply a heat transfer fluid to the catheter;
　a single-use, disposable pump adapted to pump heat transfer fluid through said catheter from said fluid reservoir;
　a single-use, disposable filter assembly adapted to remove impurities from said heat transfer fluid;
　a single-use, disposable heat exchanger member adapted for use with a multi-use, non-disposable heat exchanger for transferring heat between said heat exchanger and said fluid;
　a single-use, disposable temperature and pressure sensor block member for use with a multi-use, non-disposable temperature and pressure sensor electronics member;
　a single-use, disposable supply line communicating said fluid reservoir, pump, filter assembly, heat exchanger, and temperature and pressure sensor block member, and adapted to be connected to said catheter for supplying heat transfer fluid to said catheter; and
　a single-use, disposable return line communicating said temperature and pressure sensor block member and fluid reservoir, and adapted to be connected to said catheter for returning heat transfer fluid to said fluid reservoir;

connecting said return line and supply line to said catheter;

coupling said single-use, disposable temperature and pressure sensor block member with said multi-use, non-disposable temperature and pressure sensor electronics member;

coupling said single-use, disposable heat exchanger member with said multi-use, non-disposable heat exchanger;

circulating heat transfer fluid and controlling the flow rate and temperature of the same through said catheter with said pump, heat exchanger, and said temperature and pressure sensor block member and electronics member;

disposing said circulation set after a single use, wherein said heat exchanger member is an IV bag adapted to be removably disposed between a pair of heat exchanger molds.

26. The method of claim 25, wherein said IV bag is adapted to be shaped into a serpentine heat transfer fluid path.

27. A disposable fluid reservoir for supplying a heat transfer fluid to a circulation set of a heat transfer catheter, the circulation set including a supply line for supplying heat transfer fluid to said heat transfer catheter for fluid circulation purposes and a return line for returning heat transfer fluid to said fluid reservoir for fluid circulation purposes, the fluid reservoir comprising:

an intravenous ("IV") bag normally used for the intravenous delivery of one or more fluids to the vasculature of a patient, said bag including a top and a bottom;

an inlet line located within said bag and adapted to communicate with said return line for returning fluid to said bag during circulation; and an outlet line located within said bag and adapted to communicate with said supply line for supplying fluid to said catheter during circulation.

28. The fluid reservoir of claim 27, wherein said IV bag includes an air-removal mechanism.

29. A fluid reservoir for supplying a heat transfer fluid to a circulation set of a heat transfer catheter, the circulation set including a supply line for supplying heat transfer fluid to said heat transfer catheter for fluid circulation purposes and a return line for returning heat transfer fluid to said fluid reservoir for fluid circulation purposes, the fluid reservoir comprising:

a fluid reservoir body including a top and a bottom;

an air-removal mechanism located in the body near the top of said body;

an inlet line including an outlet located within said body, said inlet line adapted to communicate with said return line for returning fluid to said body during circulation;

an outlet line including an inlet located at least partially within said body, said outlet line adapted to communicate with said supply line for supplying fluid to said catheter during circulation; and wherein the outlet of the inlet line is located closer to said air-removal mechanism than the inlet of said outlet line.

30. The reservoir of claim 29, wherein the outlet of said return line is located adjacent to said air-removal mechanism.

31. A method of using a fluid reservoir in a circulation set for a heat transfer catheter, the circulation set including a supply line for supplying heat transfer fluid to said catheter for fluid circulation purposes and a return line for returning heat transfer fluid to said fluid reservoir for fluid circulation purposes, the method comprising:

using intravenous ("IV") bag normally used for the intravenous delivery of one or more fluids to the vasculature of a patient as a fluid reservoir in a circulation set for a heat transfer catheter, an inlet line located within said IV bag and adapted to communicate with said return line for returning fluid to said IV bag during circulation, and an outlet line located within said IV bag and adapted to communicate with said supply line for supplying fluid to said catheter during circulation;

circulating heat transfer fluid from said catheter through said return line, into said inlet line, through said IV bag, out said outlet line, and through said supply line to said catheter;

disposing said IV bag after a single use.

32. The method of claim 31, wherein said IV bag includes an air-removal mechanism and the method further includes removing air from said circulation set with said air-removal mechanism.

33. A method of using a fluid reservoir in a circulation set for a heat transfer catheter, the circulation set including a supply line for supplying heat transfer fluid to said catheter for fluid circulation purposes and a return line for returning heat transfer fluid to said fluid reservoir for fluid circulation purposes, the method comprising:

providing a fluid reservoir, the fluid reservoir comprising:
a fluid reservoir body;
an air-removal mechanism located in the body;
an inlet line including an outlet located within said body, said inlet line adapted to communicate with said return line for returning fluid to said body during circulation;
an outlet line including an inlet located at least partially within said body, said outlet line adapted to communicate with said supply line for supplying fluid to said catheter during circulation; and
wherein the outlet of the inlet line is located closer to said air-removal mechanism than the inlet of said outlet line;

circulating heat transfer fluid from said catheter through said return line, into said inlet line, through said fluid reservoir body, out said outlet line, and through said supply line to said catheter;

removing air from the circulation set with said air-removal mechanism.

34. The method of claim 33, wherein the outlet of said return line is located adjacent to said air-removal mechanism.

35. A temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from said catheter for fluid circulation purposes, the temperature and pressure sensor assembly comprising:

a multi-use, non-disposable temperature and pressure sensor electronics member;

a single-use, disposable temperature and pressure sensor block member removably coupled to said electronics member so that said block member may be discarded after a single use and said electronics member may be used multiple times with different disposable block assemblies, said block member adapted to communicate with said supply line and return line, wherein said single-use, disposable temperature and pressure sensor block member includes a block made of polycarbonate.

36. A temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from said catheter for fluid circulation purposes, the temperature and pressure sensor assembly comprising:

a multi-use, non-disposable temperature and pressure sensor electronics member;

a single-use, disposable temperature and pressure sensor block member removably coupled to said electronics member so that said block member may be discarded after a single use and said electronics member may be used multiple times with different disposable block assemblies, said block member adapted to communicate with said supply line and return line, wherein said single-use, disposable temperature and pressure sensor block member includes a pressure sensor hole in communication with said supply lumen and adapted to receive a pressure sensor of said electronics member, a temperature sensor hole in communication with said supply lumen and adapted to receive a temperature sensor of said electronics member, a pressure sensor hole in communication with said return lumen and adapted to receive a pressure sensor of said electronics member, and a temperature sensor hole in communication with said return lumen and adapted to receive a temperature sensor of said electronics member.

37. A temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from said catheter for fluid circulation purposes, the temperature and pressure sensor assembly comprising:

a multi-use, non-disposable temperature and pressure sensor electronics member;

a single-use, disposable temperature and pressure sensor block member removably coupled to said electronics member so that said block member may be discarded after a single use and said electronics member may be used multiple times with different disposable block assemblies, said block member adapted to communicate with said supply line and return line, wherein said electronics member includes a pressure sensor adapted to be operatively associated with said supply lumen for measuring the pressure of said heat transfer fluid entering said catheter, a temperature sensor adapted to be operatively associated with said supply lumen for measuring the temperature of said heat transfer fluid entering said catheter, a pressure sensor adapted to be operatively associated with said return lumen for measuring the pressure of said heat transfer fluid exiting said catheter, and a temperature sensor adapted to be operatively associated with said return lumen for measuring the temperature of said heat transfer fluid exiting said catheter.

38. A temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from said catheter for fluid circulation purposes, the temperature and pressure sensor assembly comprising:

a multi-use, non-disposable temperature and pressure sensor electronics member;

a single-use, disposable temperature and pressure sensor block member removably coupled to said electronics member so that said block member may be discarded after a single use and said electronics member may be used multiple times with different disposable block assemblies, said block member adapted to communicate with said supply line and return line, further including a single-use, disposable temperature sensor coupler adapted to be received by said temperature sensor and communicate with said heat transfer fluid via said temperature sensor holes, said coupler made of a material having a high thermal conductivity so that said temperature sensor accurately senses the temperature of said heat transfer fluid without contacting said heat transfer fluid.

39. A temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from said catheter for fluid circulation purposes, the temperature and pressure sensor assembly comprising:

a multi-use, non-disposable temperature and pressure sensor electronics member;

a single-use, disposable temperature and pressure sensor block member removably coupled to said electronics member so that said block member may be discarded after a single use and said electronics member may be used multiple times with different disposable block assemblies, said block member adapted to communicate with said supply line and return line, further including a single-use, disposable pressure sensor membrane disposed in said pressure sensor hole and adapted to be operatively associated with said pressure sensor and communicate with said heat transfer fluid to sense the pressure of said heat transfer fluid without contacting it.

40. A single-use, disposable temperature and pressure sensor block member of a temperature and pressure sensor assembly of a circulation set of a heat transfer catheter for measuring temperature and pressure of a heat transfer fluid flowing through a supply line for supplying heat transfer fluid to a catheter for fluid circulation purposes and a return line for returning heat transfer fluid from said catheter for fluid circulation purposes, the temperature and pressure sensor block member comprising:

a single-use, disposable temperature and pressure sensor block member adapted to be removably coupled to a multi-use, non-disposable temperature and pressure sensor electronics member so that said block member may be discarded after a single use and said electronics member may be used multiple times with different disposable block assemblies, said block member including a pressure sensor hole adapted to communicate with a supply lumen and receive a pressure sensor of said electronics member, a temperature sensor hole adapted to communicate with said supply lumen and receive a temperature sensor of said electronics member, a pressure sensor hole adapted to communicate with a return lumen and receive a pressure sensor of said electronics member, and a temperature sensor hole adapted to communicate with said return lumen and receive a temperature sensor of said electronics member.

41. The block member of claim 40, wherein said single-use, disposable temperature and pressure sensor block member includes a block made of polycarbonate.

42. The block member of claim 40, further including a single-use, disposable temperature sensor coupler adapted to be received by said temperature sensor and communicate with said heat transfer fluid via said temperature sensor hole, said coupler made of a material having a high thermal conductivity so that said temperature sensor accurately senses the temperature of said heat transfer fluid without contacting said heat transfer fluid.

43. The block member of claim 40, further including a single-use, disposable pressure sensor membrane disposed in said pressure sensor hole and adapted to be operatively associated with said pressure sensor and communicate with said heat transfer fluid to sense the pressure of said heat transfer fluid without contacting it.

44. A method of using a single-use, disposable temperature and pressure sensor block member of a temperature and pressure sensor assembly of a circulation set for a heat transfer catheter, the method comprising:

removably attaching a single-use, disposable temperature and pressure sensor block member of a temperature and pressure sensor assembly to a multi-use, non-disposable temperature and pressure sensor electronics member;

coupling said single-use, disposable temperature and pressure sensor block member to said heat transfer catheter;

circulating heat transfer fluid through said block member and heat transfer catheter;

sensing temperature and pressure of heat transfer fluid flowing through said block member;

disposing said block member but not said electronics member after a single use of said heat transfer catheter.

45. A method of using a single-use, disposable temperature and pressure sensor block member of a temperature and pressure sensor assembly of a circulation set for a heat transfer catheter, the method comprising:

removably attaching a single-use, disposable temperature and pressure sensor block member of a temperature and pressure sensor assembly to a multi-use, non-disposable temperature and pressure sensor electronics member, said block member including a supply lumen adapted to be coupled to said heat transfer catheter for delivery of heat transfer fluid thereto, a return lumen adapted to be coupled to said heat transfer catheter for delivery of heat transfer fluid therefrom, a pressure sensor hole adapted to communicate with said supply lumen and receive a sensor of said electronics member, a temperature sensor hole adapted to communicate with said supply lumen and receive a temperature sensor of said electronics member, a pressure sensor hole adapted to communicate with said return lumen and receive a pressure sensor of said electronics member, and a temperature sensor hole adapted to communicate with said return lumen and receive a temperature sensor of said electronics member;

coupling the supply lumen and return lumen of said block member with said heat transfer catheter;

circulating heat transfer fluid through said supply lumen of said block member, heat transfer catheter, and return lumen of said block member;

sensing temperature and pressure of heat transfer fluid flowing through said supply lumen of said block member with said temperature and pressure sensors of said electronics member and sensing temperature and pressure of heat transfer fluid flowing through said return lumen of said block member with said temperature and pressure sensors of said electronics member;

disposing said block member but not said electronics member after a single use of said heat transfer catheter.

46. The method of claim 45, wherein said single-use, disposable temperature and pressure sensor block member includes a block made of polycarbonate.

47. The method of claim 45, further including a single-use, disposable temperature sensor coupler adapted to be received by said temperature sensor and communicate with said heat transfer fluid via said temperature sensor hole, said coupler made of a material having a high thermal conductivity so that said temperature sensor accurately senses the temperature of said heat transfer fluid without contacting said heat transfer fluid.

48. The method of claim 45, further including a single-use, disposable pressure sensor membrane disposed in said pressure sensor hole and adapted to be operatively associated with said pressure sensor and communicate with said heat transfer fluid to sense the pressure of said heat transfer fluid without contacting it.

49. A method of using a heat exchanger member in a circulation set for a heat transfer catheter, the circulation set including a heat exchanger adapted to transfer heat between the heat exchanger and heat transfer fluid within the heat exchanger member for temperature control of the heat transfer fluid, the method comprising:

providing a single-use, disposable heat exchanger member with said heat exchanger, said heat exchanger member including at least one passage adapted to allow heat transfer fluid to flow therethrough;

transferring heat between said heat exchanger and said heat transfer fluid in said heat exchanger member, either to said heat transfer fluid from said heat exchanger or from said heat transfer fluid to said heat exchanger;

disposing of said heat exchanger member, but not said heat exchanger after a single use of said heat transfer catheter.

50. The method of claim 49, wherein said heat exchanger member is adapted to be used with a dry heat exchanger so that an outer surface of said heat exchanger member does not contact a heat exchanger liquid.

51. The method of claim 49, wherein said heat exchanger member is an IV bag adapted to be removably disposed between a pair of heat exchanger molds.

52. The method of claim 51, wherein said IV bag is adapted to be shaped into a serpentine heat transfer fluid path by a pair of heat exchanger molds, and said step of providing said heat exchanger member with said heat exchanger includes providing said heat exchanger member between said pair of heat exchanger molds and molding said IV bag so as to include a serpentine heat transfer fluid path.

53. A heat exchanger of a circulation set for a heat transfer catheter, comprising:

a pair of heat exchanger mold members each including an insulative body with an inner surface, a heat conductive face bonded to the inner surface of said face, and one or more heat transfer liquid paths located between said inner surface of said insulative body and said heat conductive face, the heat conductive face including a mold configuration and adapted, when placed together with the opposite face, to receive a disposable heat exchanger member and shape said disposable heat exchanger member into one or more heat transfer paths for transferring a heat transfer fluid therethrough.

54. The heat exchanger of claim 53, wherein said heat conductive faces are adapted to isolate said heat transfer liquid from an outer surface of said heat exchanger member.

55. The heat exchanger of claim 53, wherein said heat conductive faces are adapted to receive an IV bag and shape said IV bag into one or more heat transfer paths.

56. The heat exchanger of claim 55, wherein said heat conductive faces are adapted to shape said IV bag into a serpentine heat transfer fluid path.

57. A method of identifying a heat transfer catheter or heat transfer element of a heat transfer catheter, comprising:

measuring catheter pressure at a variety of heat transfer fluid flow rates;

determining a slope of a best fit line through a variety of data points determined by said measuring step;

identifying the heat transfer catheter or heat transfer element by comparing the slope determined by said determining step to established slopes for a variety of different heat transfer catheters or heat transfer elements.

58. The method of claim 57, further including controlling one or more operational parameters of the catheter or heat transfer element based on the heat transfer catheter or heat transfer element identified.

* * * * *